US006436389B1

(12) United States Patent
Gage et al.

(10) Patent No.: US 6,436,389 B1
(45) Date of Patent: Aug. 20, 2002

(54) STIMULATION OF CELL PROLIFERATION BY GLYCOSYLATED CYSTATIN C

(75) Inventors: Fred Harrison Gage; Philippe J. Taupin, both of La Jolla; Jasodhara Ray, San Diego, all of CA (US)

(73) Assignee: The Salk Institute for Biological Studies, La Jolla, CA (US)

( * ) Notice: Subject to any disclaimer, the term of this patent is extended or adjusted under 35 U.S.C. 154(b) by 0 days.

(21) Appl. No.: 09/459,958

(22) Filed: Dec. 13, 1999

Related U.S. Application Data

(63) Continuation-in-part of application No. 09/210,344, filed on Dec. 11, 1998, now abandoned.

(51) Int. Cl.[7] ........................ A61K 38/00; A61K 45/00; C07K 14/00; C12N 5/00

(52) U.S. Cl. ........................ 424/85.1; 424/198.1; 435/4; 435/325; 435/375; 435/377; 514/2; 514/12; 530/350; 530/399

(58) Field of Search ............................ 424/198.1, 85.1; 435/325, 352, 366, 377, 4, 375; 514/2, 12; 530/300, 350, 399

(56) References Cited

U.S. PATENT DOCUMENTS

| | | | | |
|---|---|---|---|---|
| 5,733,893 A | * | 3/1998 | Ornitz et al. | 514/56 |
| 5,766,948 A | * | 6/1998 | Gage et al. | 435/368 |
| 5,851,832 A | * | 12/1998 | Weiss et al. | 435/368 |
| 5,980,885 A | * | 11/1999 | Weiss et al. | 424/93.21 |

OTHER PUBLICATIONS

Galzie et al. Fibroblast growth factors and their receptors. Biochem Cell Biol 75: 669–685, 1997.*
Palmer et al. Progenitor cells from human brain after death. Nature 411: 42–43, 2001.*
Palmer et al. Fibroblast growth factor–2 activates a latent neurogenic program in neural stem cells from diverse regions of the adult CNS. J Neurosci 19(19): 8487–84978, 1999.*
Walz et al. Essential role of heparan sulfates in axon navigatioin and targeting in the developing visual system. Development 124: 2421–2430, 1997.*
Fagan et al. Endogenous FGF–2 is important for cholinergic sprouting in the denervated hippocampus. J Neurosci 17(7): 2499–2511, 1997.*
Kawada et al. Stimulation fo human keratinocyte growth by alginate oligosaccharides, a possible co–factor for epidermal growth factor in cell culture. FEBS Letters 708: 43–46, 1997.*
Yayon et al. Cell surfacem heparin–like molecules are required for binding of basic fibroblast growth factor ot its high affinity receptor. Cell 64: 841–848, 1991.*
Ornitz et al. Heparin is required for cell–free binding of basic fibroblast growth factor to a soluble receptor and for mitogenesis in whole cells. Mol Cell Biol 12: 240–247, 1992.*
Wagner et al. Stimulation of neonatal and adult brain neurogenesis by subcutaneous injection of basic fibroblast growth. J Neurosci 19(4): 6006–6014, 199.*
Kuhn et al. Epidermal growth factor and fibroblast growth factor–2 have different effects on neural progenitors in the adult rat brain. J Neurosci 17(15): 5820–5829, 1997.*
Grothe et al. Fibroblast growth factor and its implications for developing and regenerating neurons. Int J Dev Biol 40: 403–410 1996.*
Gage et al. Survival and differentiation of adult neuronal progenitor cells transplanted to the adult brain. Proc Natl Acad Sci USA 92: 11879–11883, 1995.*
Ngo et al. Computational complexity, protein structure prediction, and the Levinthal paradox. The Protein Folding Problem and Tertiary Structure Prediction, pp. 492–495, 1995.*
Skolnick et al. From genes to protein structure and function: novel applications of computational approaches in the genomic era. Trends in Biotech 18(1): 34–39, 2000.*
Bork, A. Powers and pitfalls in sequence analysis: the 70% hurdle. Genome Res 10: 398–400, 2000.*
Doerks et al. Protein annotation: detective work for function prediction. Trends in Genetics 14(6): 248–250, 1998.*
Smith et al. The challenges of genome sequence annotation or "The devil is in the details". Nature Biotech 15: 1222–1223, 1997.*
Brenner, S.E. Errors in genome function. Trends in Genetics 15(4): 132–133, 1999.*
Wells. J.A. Additivity of mutational effects in proteins. Biochemistry 29 (37): 8509–8517, 1990.*
Bork et al. Go hunting in sequence databases but watch out for the traps. Trends in Genetics. 12(10): 425–427, 1996.*
Taupin et al. FGF–2–responsive neural stem cell proliferation requires CCg, a novel autocrine/paracrine cofactor. Neuron 28: 385–297, 2000.*

\* cited by examiner

*Primary Examiner*—Gary L. Kunz
*Assistant Examiner*—Bridget E. Bunner
(74) *Attorney, Agent, or Firm*—Knobbe, Martens, Olson & Bear, LLP

(57) ABSTRACT

The present invention is based on the discovery and isolation of a co-factor for trophic factors. It has been discovered that trophic factors require a co-factor to stimulate and/or potentiate the trophic factor activity and/or specificity. This was clearly identified in low density cells where trophic factors are unable, or at best, at minimal levels, able to proliferate undifferentiated cells without a co-factor. In a particular embodiment of the present invention, there is provided a composition comprising glycosylated cystatin C, (CCg), an FGF co-factor that stimulates proliferation of neural and fibroblast associated undifferentiated cells. The N-glycosylation of cystatin C is required for its activity. Moreover, CCg acts in cooperation with basic fibroblast growth factor (FGF-2) to induce neural progenitor cell proliferation.

12 Claims, 9 Drawing Sheets

| Sample | Digest | Peptide | Sequence | Experimental mass (Da, 1) | Theoretical mass (Da, 2) | Difference (1) - (2) |
|---|---|---|---|---|---|---|
| 21 kDa | tryptic | G1749 | LLGAPQEADASEEGVQR | nd | 1,769.8 | |
| | | G1615 | (L)(L)GAPQEADASE(E)GV | 1,766.6 | 2,244.0 | |
| | | G1748 | ALDFA(V)SEYNKGNDAYH | 2,242.8 | 2,618.3 | |
| | | G1750 | (G)XSR(P)(P)RLLGA(P)QEADA | 2,962 | 12,480.1 | 342 |
| | | G1751 | LLGAXQEADASXE(D,G)VQRALDFAV(S)(E)YNK(G)XNDA | 14,494 | 13,329.1 | 2,014 |
| | | G1752 | (G)X(S,C)(A,R)P(P)XRLLGAXQ(E)AD(A) | 16,125 | 2,483.1 | 2,796 |
| | Asp-N | G1754 | DVEMGR(T)XXXK(S,C)QXX(L) | 4,264.4 / 5,060.3 | 3,875.9 | 1,781.3 / 2,577.2 |
| | | G1755 | (D)QPHL | 3,878.4 | | |

*FIG. 2A*

| | DIV 1 | DIV 3 | DIV 5 | DIV 10 | DIV 15 | >DIV 15 |
|---|---|---|---|---|---|---|
| N2 | 98 (1) | 27 (3.2 ± 1.0) | 3 (2.3 ± 0.3) | 0 (-) | 0 (-) | 0 (-) |
| N2 + FGF-2 | 80 (1) | 23 (2.8 ± 0.3) | 11 (6.0 ± 2.7) | 3 (23.0 ± 19.5) | 1 (55) | 0 (-) |
| N2 + CCg | 21 (1) | 17 (2.2 ± 0.2) | 16 (5.2 ± 1.4) | 5 (11.6 ± 5.9) | 1 (5) | 0 (-) |
| N2 + FGF-2 +CCg | 19 (1) | 14 (5.5 ± 1.7) | 11 (15.0 ± 5.0) | 6 (67 ± 18.6) | 6 (247.1 + 52.5) | 6 passaged |

*FIG. 7*

|  | Cell number | | | |
|---|---|---|---|---|
|  | no FGF-2 | | + FGF-2 (20 ng/ml) | |
| Trophic factor/cytokine | DIV 1 | DIV 5 | DIV 1 | DIV 5 |
| FGF-2 (20 ng/ml) | 15.3 ± 0 | 6.6 ± 3 | 42.1 ± 12 | 3.6 ± 1 |
| FGF-2 (100 ng/ml) | 41.7 ± 11 | 2.9 ± 1 | | |
| Heparin (2 μg/ml) | 14.6 ± 2 | 3.0 ± 0 | 10.6 ± 2 | 2.0 ± 2 |
| FGF-1 (40 ng/ml) | 31.6 ± 1 | 0.3 ± 0 | 34.3 ± 8 | 0.6 ± 0 |
| FGF-4 (40 ng/ml) | 31.6 ± 2 | 6.0 ± 2 | 25.3 ± 2 | 0.0 ± 0 |
| FGF-7 (20 ng/ml) | 14.6 ± 2 | 8.0 ± 2 | 14.6 ± 0 | 8.0 ± 2 |
| NGF (50 ng/ml) | 35.5 ± 9 | 8.8 ± 5 | 33.3 ± 12 | 5.9 ± 3 |
| BDNF (20 ng/ml) | 36.4 ± 14 | 5.4 + 5 | 38.9 ± 12 | 5.6 ± 8 |
| NT-3 (40 ng/ml) | 30.6 ± 0 | 1.0 ± 0 | 28.3 ± 2 | 2.0 ± 1 |
| EGF (40 ng/ml) | 39.3 ± 3 | 0.6 ± 0 | 36.6 ± 1 | 2.0 ± 1 |
| CNTF (40 ng/ml) | 25.3 ± 2 | 0.6 ± 0 | 25.0 ± 1 | 0.3 ± 0 |
| PDGF (40 ng/ml) | 23.3 ± 2 | 0.0 ± 0 | 17.1 ± 1 | 0.0 ± 0 |
| GDNF (20 ng/ml) | 16.6 ± 2 | 0.0 ± 0 | 19.6 ± 2 | 0.0 ± 0 |
| IL-3 (20 ng/ml) | 32.0 ± 4 | 1.6 ± 0 | 20.6 ± 6 | 1.3 ± 0 |
| IL-4 (20 ng/ml) | 50.6 ± 3 | 2.3 ± 0 | 46.3 ± 3 | 9.0 ± 5 |
| IL-6 (20 ng/ml) | 18.0 ± 4 | 1.6 ± 0 | 18.6 ± 6 | 0.3 ± 0 |
| TNF-α (10 ng/ml) | 37.9 ± 9 | 7.3 ± 0 | 37.9 ± 8 | 9.0 ± 4 |
| PTN (20 ng/ml) | 20.3 ± 2 | 0.0 ± 0 | 24.6 ± 4 | 2.3 ± 2 |
| Activin (20 ng/ml) | 26.3 ± 0 | 0.0 ± 0 | 37.6 ± 5 | 0.0 ± 0 |
| TGF-α (40 ng/ml) | 21.3 ± 4 | 1.0 ± 0 | 17.6 ± 3 | 0.6 ± 0 |
| TGF-β (20 ng/ml) | 26.0 ± 3 | 0.0 ± 0 | 36.3 ± 3 | 0.0 ± 0 |
| IGF-I (20 ng/ml) | 16.0 ± 2 | 2.6 ± 1 | 17.3 ± 3 | 0.0 ± 0 |
| IGF-II (20 ng/ml) | 17.0 ± 1 | 2.0 ± 1 | 21.0 ± 4 | 2.6 ± 0 |
| MIP-1α (6 ng/ml) | 11.6 ± 2 | 0.3 ± 0 | 12.0 ± 0 | 0.3 ± 0 |
| MIP-1β (40 ng/ml) | 13.6 ± 2 | 1.0 ± 0 | 19.3 ± 0 | 0.3 ± 0 |
| Rantes (20 ng/ml) | 20.6 ± 5 | 0.0 ± 0 | 18.0 ± 2 | 0.0 ± 0 |
| SCF (20 ng/ml) | 28.0 ± 4 | 5.1 ± 0 | 10.6 ± 6 | 0.5 ± 0 |

FIG. 6

SEQUENCE LISTING

```
<160> NUMBER OF SEQ ID NOS:  15

<210> SEQ ID NO 1
<211> LENGTH: 18
<212> TYPE: PRT
<213> ORGANISM: Rattus norvegicus
<220> FEATURE:
<221> NAME/KEY: VARIANT
<222> LOCATION: 2,4-8,13,15
<223> OTHER INFORMATION: Xaa = Any Amino Acid; could not be determined
      with greater than 50% certainty.

<400> SEQUENCE: 1

Gly Xaa Ser Xaa Xaa Xaa Xaa Xaa Leu Leu Gly Ala Xaa Gln Xaa Ala
 1               5                  10                  15

Asp Ala

<210> SEQ ID NO 2
<211> LENGTH: 17
<212> TYPE: PRT
<213> ORGANISM: Rattus norvegicus

<400> SEQUENCE: 2

Leu Leu Gly Ala Pro Gln Glu Ala Asp Ala Ser Glu Glu Gly Val Gln
 1               5                  10                  15

Arg

<210> SEQ ID NO 3
<211> LENGTH: 15
<212> TYPE: PRT
<213> ORGANISM: Rattus norvegicus
<220> FEATURE:
<221> NAME/KEY: VARIANT
<222> LOCATION: 1,2,13
<223> OTHER INFORMATION: less than 70% confidence

<400> SEQUENCE: 3

Leu Leu Gly Ala Pro Gln Glu Ala Asp Ala Ser Glu Glu Gly Val
 1               5                  10                  15

<210> SEQ ID NO 4
<211> LENGTH: 17
<212> TYPE: PRT
<213> ORGANISM: Rattus norvegicus
<220> FEATURE:
```

```
<221> NAME/KEY: VARIANT
<222> LOCATION: 6
<223> OTHER INFORMATION: less than 70% confidence

<400> SEQUENCE: 4

Ala Leu Asp Phe Ala Val Ser Glu Tyr Asn Lys Gly Asn Asp Ala Tyr
 1               5                  10                  15
His

<210> SEQ ID NO 5
<211> LENGTH: 18
<212> TYPE: PRT
<213> ORGANISM: Rattus norvegicus
<220> FEATURE:
<221> NAME/KEY: VARIANT
<222> LOCATION: 1,5,6,7,13
<223> OTHER INFORMATION: less than 70% confidence
<221> NAME/KEY: VARIANT
<222> LOCATION: 2
<223> OTHER INFORMATION: Xaa = Any Amino Acid; could not be determined
      with greater than 50% certainty

<400> SEQUENCE: 5

Gly Xaa Ser Arg Pro Pro Pro Arg Leu Leu Gly Ala Pro Gln Glu Ala
 1               5                  10                  15
Asp Ala

<210> SEQ ID NO 6
<211> LENGTH: 33
<212> TYPE: PRT
<213> ORGANISM: Rattus norvegicus
<220> FEATURE:
<221> NAME/KEY: VARIANT
<222> LOCATION: 14
<223> OTHER INFORMATION: Xaa = Asp or Gly; could not make unambiguous
      assignment
<221> NAME/KEY: VARIANT
<222> LOCATION: 5,12,30
<223> OTHER INFORMATION: Xaa = Any Amino Acid; could not be determined
      with greater than 50% certainty
<221> NAME/KEY: VARIANT
<222> LOCATION: 24,25,29
<223> OTHER INFORMATION: less than 70% confidence

<400> SEQUENCE: 6

Leu Leu Gly Ala Xaa Gln Glu Ala Asp Ala Ser Xaa Glu Xaa Val Gln
 1               5                  10                  15
Arg Ala Leu Asp Phe Ala Val Ser Glu Tyr Asn Lys Gly Xaa Asn Asp
                20                  25                  30
Ala

<210> SEQ ID NO 7
<211> LENGTH: 18
<212> TYPE: PRT
<213> ORGANISM: Rattus norvegicus
<220> FEATURE:
<221> NAME/KEY: VARIANT
<222> LOCATION: 1,6,15,18
<223> OTHER INFORMATION: less than 70% confidence
<221> NAME/KEY: VARIANT
<222> LOCATION: 3
<223> OTHER INFORMATION: Xaa = Ser or Cys; could not make unambiguous
      assignment
<221> NAME/KEY: VARIANT
<222> LOCATION: 4
<223> OTHER INFORMATION: Xaa = Ala or Arg; could not make unambiguous
      assignment
<221> NAME/KEY: VARIANT
<222> LOCATION: 2,7,13
```

```
<223> OTHER INFORMATION: Xaa = Any Amino Acid; could not be determined
      with greater than 50% certainty

<400> SEQUENCE: 7

Gly Xaa Xaa Xaa Pro Pro Xaa Arg Leu Leu Gly Ala Xaa Gln Glu Ala
 1               5                  10                  15

Asp Ala

<210> SEQ ID NO 8
<211> LENGTH: 16
<212> TYPE: PRT
<213> ORGANISM: Rattus norvegicus
<220> FEATURE:
<221> NAME/KEY: VARIANT
<222> LOCATION: 7,16
<223> OTHER INFORMATION: less than 70% confidence
<221> NAME/KEY: VARIANT
<222> LOCATION: 8,9,10,14,15
<223> OTHER INFORMATION: Xaa = Any Amino Acid; could not be determined
      with greater than 50% certainty
<221> NAME/KEY: VARIANT
<222> LOCATION: 12
<223> OTHER INFORMATION: Xaa = Ser or Cys; could not make unambiguous
      assignment

<400> SEQUENCE: 8

Asp Val Glu Met Gly Arg Thr Xaa Xaa Xaa Lys Xaa Gln Xaa Xaa Leu
 1               5                  10                  15

<210> SEQ ID NO 9
<211> LENGTH: 5
<212> TYPE: PRT
<213> ORGANISM: Rattus norvegicus
<220> FEATURE:
<221> NAME/KEY: VARIANT
<222> LOCATION: 1
<223> OTHER INFORMATION: less than 70% confidence

<400> SEQUENCE: 9

Asp Gln Pro His Leu
 1               5

<210> SEQ ID NO 10
<211> LENGTH: 33
<212> TYPE: DNA
<213> ORGANISM: Artificial Sequence
<220> FEATURE:
<223> OTHER INFORMATION: oligonucleotide for PCR

<400> SEQUENCE: 10
gagagagaat tcatggccag cccgctgcgc tcc                                 33

<210> SEQ ID NO 11
<211> LENGTH: 34
<212> TYPE: DNA
<213> ORGANISM: Artificial Sequence
<220> FEATURE:
<223> OTHER INFORMATION: oligonucleotide for PCR

<400> SEQUENCE: 11
agagagatcg atggcatttt tgcagctgaa attt                                34

<210> SEQ ID NO 12
<211> LENGTH: 42
<212> TYPE: DNA
<213> ORGANISM: Artificial Sequence
<220> FEATURE:
<223> OTHER INFORMATION: oligonucleotide for PCR
```

<400> SEQUENCE: 12
gtcctgggcg tggcctgggc ggccccggag gaggcagatg cc                              42

<210> SEQ ID NO 13
<211> LENGTH: 21
<212> TYPE: DNA
<213> ORGANISM: Artificial Sequence
<220> FEATURE:
<223> OTHER INFORMATION: oligonucleotide for PCR

<400> SEQUENCE: 13
cgcccaggcc acgcccagga c                                                    21

<210> SEQ ID NO 14
<211> LENGTH: 42
<212> TYPE: DNA
<213> ORGANISM: Artificial Sequence
<220> FEATURE:
<223> OTHER INFORMATION: oligonucleotide for PCR

<400> SEQUENCE: 14
cgaactacat gtaccaagtc ccagacagat ttgactgact gt                              42

<210> SEQ ID NO 15
<211> LENGTH: 21
<212> TYPE: DNA
<213> ORGANISM: Artificial Sequence
<220> FEATURE:
<223> OTHER INFORMATION: oligonucleotide for PCR

<400> SEQUENCE: 15
ggacttggta catgtagttc g                                                    21

STIMULATION OF CELL PROLIFERATION BY GLYCOSYLATED CYSTATIN C

This is a continuation-in-part of application Ser. No. 09/210,344, filed Dec. 11, 1998, now abandoned.

STATEMENT AS TO FEDERALLY SPONSORED RESEARCH

This invention was made with partial Government support under Grant No. AG06088, award by the National Institutes of Health. The government may have certain rights in the invention.

FIELD OF THE INVENTION

The present invention relates generally to the discovery of co-factors for trophic factors which stimulates and/or potentiates the activity and/or specificity of trophic factors, methods of use thereof.

BACKGROUND OF THE INVENTION

Trophic factors have a broad range of biological activities and their activity and specificity may be achieved by cooperation with other factors. Although trophic factors are generally active at extremely low concentrations, high concentrations of mitogen together with high cell density are often required to induce proliferation of multipotent neural stem cell populations. Growth factors for early progenitors may be useful for enhancing the success of gene transfer into stem cells as well as treating disorders by renewal of mature cells from the stem cell pool. In vitro assays using recombinant neurotrophic factors have indicated that members of a neurotrophic gene family may play sequential and complementary roles during development of the adult nervous system.

Neurotropic factors that have been identified include NT-4, NT-5, NT-6, NT-7, CNTF (ciliary neuronotrophic factor ), GDNF (Glial cell line-derived neurotrophic factor), and Purpurin. NSE (neuron-specific enolase) has been found to be a neuronal survival factor. Other factors possessing a broader spectrum of functions and which have neurotrophic activities, but are not normally classified as neurotrophins, also exist. These factors include EGF (epithelial growth factor), HBNF (heparin-binding neurite-promoting factor), IGF-2, a-FGF and b-FGF , PDGF, NSE (neuron-specific enolase), and Activin A. Other factors have been identified which specifically influence neuronal differentiation and influence transmitter phenotypes without affecting neuronal survival. Although the intracerebral administration of FGF-2 has been shown to stimulate neurogenesis in the adult rat SVZ, FGF-2 alone in the adult rat hippocampus has a limited effect on the proliferation of neural stem/progenitor cells (Kuhn et al. (1997); Wagner et al. (1999) each herein incorporated by reference).

Mitogenic growth factors, like fibroblast growth factor-2 (FGF-2) (Gage, F. H., et al., 1995, *Proc. Natl Acad. Sci.* USA 92:11879–11883) and epidermal growth factor (EGF) (Lois, C., and Alvarez-Buylla, A., 1993, *Proc. Natl. Acad. Sci. USA* 90(5):2074–2077), induce proliferation of neural progenitor cells isolated from the brain. Studies from single cells in culture demonstrate that FGF-2 (Gritti, A., et al., 1996, *J. Neurosci.* 16:1091–1100) and EGF (Reynolds, B. A., and Weiss, S., 1996, *Develop. Biol.* 175:1–13) are mitogens for multipotent neural stem cells and likely cooperate with trophic factors (Cattaneo, E., and McKay, R., 1990, *Nature* 347:762–765; Stemple, D. L., and Anderson, D. J., 1992, *Cell* 71:973–985), some of which are yet unknown (Davis, A. A., and Temple, S., 1994, *Nature* 372:263–266; Temple, S., 1989, *Nature* 340:471–473; Kilpatrick, T. J., and Bartlett, P. F., 1993, *Neuron* 10:255–265; Palmer, T. D., et al., 1997, *Mol. Cell. Neurosci.* 8:389–404) to achieve specificity. There is in vitro and in vivo evidence for the existence of stem cells in the embryonic and adult brain (Altman, et al., J. Comp. Neurol. 124:319–335, 1965; Ericksson, et al., Nature Medicine, 1998, 40:1313–1317).

The trophic factors are of potential clinical interest since they influence the functional activities and survival of distinct neural populations within the peripheral and central nervous system. Many of these molecules are currently under investigation as therapeutic agents for the treatment of neurodegenerative disorders and nerve injury, either individually or in combination with other trophic factors.

Disorders of the central nervous system encompass numerous afflictions such as neurodegenerative diseases (e.g., Alzheimer's and Parkinson's), acute brain injury (e.g., stroke, head injury). In recent years, neurodegenerative disease has become an important concern due to the expanding elderly population which is at greatest risk for neurodegenerative disorders, such as Alzheimer's Disease, Multiple Sclerosis, Huntington's Disease, and Parkinson's Disease.

SUMMARY OF THE INVENTION

The present invention is based on the discovery and isolation of a co-factor for trophic factors. It has been discovered that trophic factors require a co-factor to stimulate and/or potentiate the trophic factor activity and/or specificity. This was clearly identified in low density cells where trophic factors are unable, or at best, at minimal levels, able to proliferate undifferentiated cells without a co-factor. In a particular embodiment of the present invention, there is provided a composition comprising glycosylated cystatin C, (CCg), an FGF co-factor that stimulates proliferation of neural and fibroblast associated undifferentiated cells. The N-glycosylation of cystatin C is required for its activity. Moreover, CCg acts in cooperation with basic fibroblast growth factor (FGF-2) to induce neural progenitor cell proliferation.

In a first preferred embodiment, substantially purified glycosylated cystatin C (CCg) polypeptide, and biologically active fragments thereof, are provided.

In another embodiment, a method for stimulating and/or potentiating trophic factor activity and/or specificity is provided. In a preferred embodiment, a method for inducing proliferation of a mammalian neural stem or progenitor cell is provided. This method includes contacting a neural stem or progenitor cell invention compositions, or a biologically active fragment thereof, alone or in combination with trophic factors such as fibroblast growth factor-2 (FGF-2), or a biologically active fragment thereof, under conditions that allow proliferation of the cell.

A method is also provided for inhibiting trophic factor activity and/or specificity, comprising administering inactive forms of invention polypeptides. Preferably, the present invention inhibits proliferation of a mammalian neural cell. The method includes contacting the cell with a non-glycosylated form of cystatin C (CCg) or an inhibitory peptide thereof (or of the CCg) under conditions that inhibit proliferation of the cell. In one aspect, the method further includes administering an FGF-2 inhibitory agent, such as an antibody, in addition to a non-glycosylated CCg or other inhibitory fragment of CCg.

In another embodiment, an assay system is provided for identifying co-factors for trophic factors, comprising purifying from conditioned medium a co-factor for trophic factors. The method comprises contacting cells cultured in a medium at low density, and thereafter purifying co-factors which stimulate and/or potentiate the trophic factor activity and/or specificity.

A method of identifying an agent which promotes neural cell proliferation is also provided. The method comprises contacting a neural undifferentiated cell with a test agent and with a trophic factor, such as fibroblast growth factor-2, under conditions that allow the components to interact. The ability of the neural undifferentiated cell to proliferate in the presence of the agent is compared with the ability of a neural undifferentiated cell, to proliferate in the absence of the agent.

In yet another embodiment, a method is provided for modulating FGF mediated processed comprising administering a co-factor for FGF to a subject.

In another embodiment, a method is provided for ameliorating a neural disorder in a subject by administering a therapeutically effective amount of glycosylated cystatin C to the subject.

A pharmaceutical composition is provided which contains a therapeutically effective amount of glycosylated cystatin C and a pharmaceutically acceptable carrier. In another embodiment, the composition includes FGF-2.

An antibody which binds glycosylated cystatin C with a different affinity than non-glycosylated cystatin C is further provided.

In yet another embodiment, substantially purified stem cell glycosylated cystatin C polypeptide, is provided by a method comprising purifying glycosylated cystatin C glycoprotein is also provided. The method includes, producing conditioned media from a neural progenitor or stem cell; performing affinity chromatography on the media; eluting a fraction containing mitogenic activity; performing papain chromatography on the fraction having mitogenic activity; and recovering a glycoprotein of about 21 kDa.

BRIEF DESCRIPTION OF THE DRAWINGS

FIGS. 2A–2C show the results of amino acid sequencing and mass spectral analysis. The 21 kDa protein and the peptide G1751 were digested with trypsin and endoproteinase Asp-N, respectively. The peptides, separated by HPLC, were submitted to sequencing and mass spectral analysis. FIG. 2A shows that all the sequences determined matched rat cystatin C (SEQ ID NOS:2 to 9, respectively). The peptide G1754 carries the N-linked carbohydrate moiety. Residues in parentheses were determined with less than 70% confidence. If two residues are listed in parentheses, no unambiguous assignment could be made. X denotes that no assignment could be made with >50% confidence. FIG. 2B is a plot of the mass spectral analysis. Peaks represent the different ionized forms of peptide G1751. FIG. 2C is a plot of a mass spectral analysis demonstrating the heterogeneity ofthe carbohydrate moiety of peptide G1754. m/z is the mass to charge ratio, $M^{n+}$ denotes the molecular mass of singly, doubly and triply charged species, M is the average molecular mass calculated from these charge states.

FIG. 6 is a table charting the effect of neurotrophic factors/cytokines on AHPs plated at low density.

FIG. 7 is a table providing the number of clones and average clone size.

DETAILED DESCRIPTION OF THE INVENTION

Figure 1A:
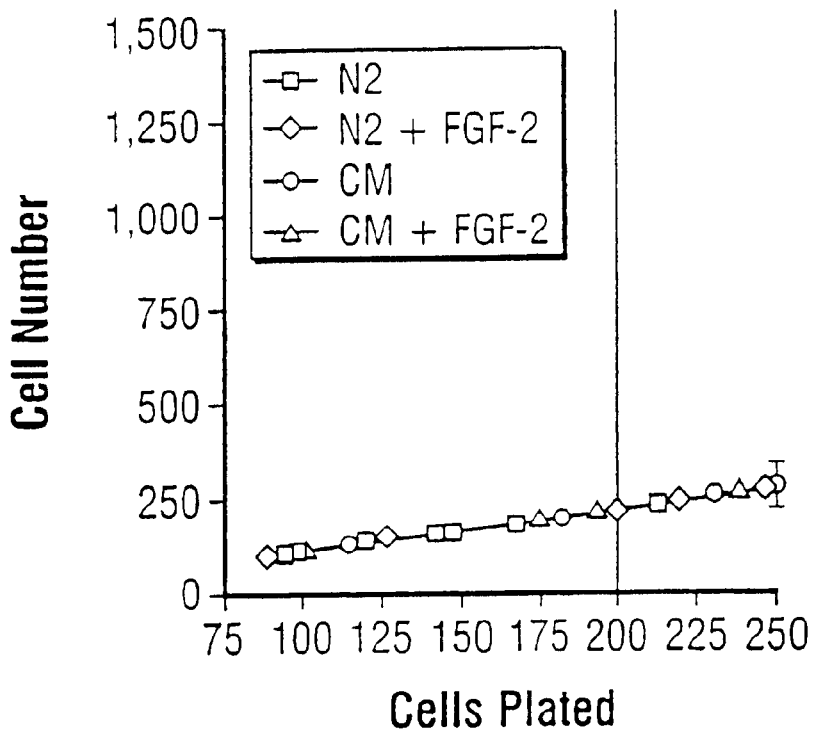
FIGS. 1A–1C show graphs of in vitro proliferation assays. AHPs, plated at different cell densities in N2, N2+FGF-2, CM and CM+FGF-2, were counted at DIV 1 (A) and DIV 5 (B). FGF-2 supports proliferation of AHPs at densities >200 cells per well; at lower densities, CM is required. The purified 21 kDa protein exhibited most of the mitogenic activity (C, fraction 11). In (C), between DIV 1 and 3 a large number of cells died, probably from the toxic compounds eluted from the membranes. Data in (A) and (B) are means ±s.e.m. of 6 independent experiments and in (C) are the means of triplicate from one of 2 typical independent experiments.

It is noted that as used herein and in the appended claims, the singular forms "a," "and," and "the" include plural referents unless the context clearly dictates otherwise. Thus, for example, reference to "a cell" includes a plurality of such cells and reference to "the cytokine" includes reference to one or more cytokines and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference in full for the purpose of describing and disclosing the cell lines, antibodies, and methodologies which are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

In a preferred embodiment of the present invention, there are provided a pharmaceutical formulation comprising a co-factor for a trophic factor and a pharmaceutically acceptable carrier, more preferably, a pharmaceutical formulation further comprising a trophic factor. As used herein, the term "co-factors" refer to factors that stimulate and/or potentiate the activity and/or specificity of trophic factors, of their target cells. It has been discovered by the present inventors that trophic factor activity and/or specificity requires or is enhanced by certain co-factors purified from the conditioned medium of cell cultures, preferably an autocrine/paracrine co-factor. For example, it has been identified that an autocrine/paracrine co-factor, purified from neural cell cultures, cooperates with fibroblast growth factor to stimulate the proliferation of neural stem cells in vitro and neurogenesis in vivo. Those of skill in the art will readily recognize additional co-factors, which can be readily identified and purified employing the methods described herein, based on the trophic factor and the conditioned medium therefor.

As used herein, the term "trophic factor" refers to compounds with trophic actions that promote and/or control proliferation, differentiation, migration, and survival (sometimes even the death) of their target cells. Such factors include cytokines, neurotrophins, epidermal growth factor, fibroblast growth factor, platelet-derived growth factor, insulin-like growth factors, ciliary neurotrophic factor and related molecules, glial-derived growth factor and related molecules, schwanoma-derived growth factor, glial growth factor, stiatal-derived neuronotrophic factor, platelet-derived growth factor, hepatocyte growth factor, scatter factor (HGF-SF), transforming growth factor-beta and related molecules, neurotransmitters, and hormones. Those of skill in the art will readily recognize additional trophic factors which can be employed in the present invention (see, e.g., Lenfant et al., Growth Factors of the Vascular and Nervous Systems: Functional Characterization and Biotechnology: International Symposium on Biotechnology of Grow (S. Karger Publishing, 1992); Aebischer et al. Neurotrophic Factors (Handbook of Experimental Pharmacology, Vol 134) (Springer Verlag, 1998); Meyers, R. A. Encyclopedia of Molecular Biology and Molecular Medicine: Denaturation of DNA—Growth Factors (VCH Pub, 1996); Meager & Robinson, Growth Factors: Essential Data (John Wiley and Sons, 1999); McKay & Brown, Growth Factors and Receptors: A Practical Approach (Oxford University Press, 1998); Leroith & Bondy, Growth Factors and Cytokines in Health and Disease, Vol 1A and 1B: A Multi-Volume Treatise (JAI Pr, 1996).

As used herein, the term "neurotrophin" or "neurotrophic factor" refers to a trophic factor that promote the survival and functional activity of nerve or glial cells, including a factor which enhances neural differentiation, induces neural proliferation, influences synaptic finctions, and/or promotes the survival of neurons that are normally destined to die, during different phases of the development of the central and peripheral nervous system. Exemplary neurotrophins includes, for example, ciliary neurotrophic factor (CNF), nerve growth factor (NGF), fibroblast growth factor (FGF), brain-derived neurotrophic factor (BDNF), Neurotrophin-3 (NT-3), glia derived neurotrophic factor (GDNF), and the like. Such factors are characterized by their trophic actions, their expression patterns in the brain, and molecular aspects of their receptors and intracellular signaling pathways.

In a preferred embodiment of the present invention, the invention co-factor is the glycosylated form of Cystatin C or glycosylated Cystatin C (CCg), which interacts and/or cooperates with trophic factors, such as FGF, to stimulate or enhance the activity and/or specificity of the trophic factor. In a more particular embodiment, the present invention is directed to the purification and characterization of the co-factor, CCg, from the conditioned medium of neural undifferentiated cell cultures and which is required for FGF-2's mitogenic activity on neural stem cells. The glycosylated form of cystatin C (CCg) is an autocrine/paracrine co-factor, whose glycosylation, such as N-glycosylation, is preferably required for its activity.

In a preferred embodiment of the present invention, CCg acts in cooperation with trophic factors to stimulate and/or potentiate the activity and/or specificity of the trophic factor. For example, CCg cooperates with members of the FGF family, such as basic fibroblast growth factor (FGF-2). FGF-2 is an 18 kDa protein with a length of 155 amino acids and an isoelectric point of 9.6. FGF-2 does not contain disulfide bonds and is not glycosylated. Variants with a length of 131 and 146 amino acids, respectively, have been described, as have higher molecular weight forms (for a review of FGF-2, see Baird, A., and Klagsbrun, M., 1991, *Cancer Cells* 3:239–43, herein incorporated by reference). The present invention also includes a composition comprising a cell proliferative amount of CCg in combination with FGF-2. One of skill in the art can determine effective amounts of CCg and FGF-2 in a mixture using the proliferation assay described in the Examples below. Alternatively, CCg can act cooperatively with other members of the FGF family. The fibroblast growth factor family includes at least seven polypeptides that have been shown to stimulate proliferation in various cell lines including endothelial cells, fibroblasts, smooth muscle cells and epidermal cells. Included in this group are acidic fibroblast growth factor (FGF-1), basic fibroblast growth factor (FGF-2), int-2 (FGF-3), Kaposi sarcoma growth factor (FGF-4), hst-1 (FGF-5), hst-2 (FGF-6) and keratinocyte growth factor; (FGF-7) (Baird and Klagsbrun, Ann. N.Y. Acad. Sci. 638: xiv, 1991).

The invention provides substantially purified CCg polypeptide. Preferably, CCg has the amino acid sequence set forth in SEQ ID NO:1. Full length, wild-type, CCg polypeptide is a glycoprotein of approximately 21 kDa. The term "substantially purified" as used herein refers to a glycoprotein or a polypeptide which is substantially free of other proteins, lipids, carbohydrates or other materials with which it is naturally associated. One skilled in the art can purify CCg using the methods set forth in the Examples, or other standard techniques for protein purification (see Barret, A. J., 1981, *Methods Enzymol.* 80:771–778, herein incorporated by reference). The substantially pure polypeptide will yield a single major band on a non-reducing polyacrylamide gel. The purity of the CCg glycoprotein can also be determined by amino-terminal amino acid sequence analysis.

The invention includes functional polypeptide, as well as functional peptide fragments thereof. As used herein, the term "functional polypeptide" refers to a polypeptide, respectively, which possesses biological function or activity which is identified through a defined functional assay and which is associated with a particular biologic, morphologic, or phenotypic alteration in the cell. A "fragment" is a polypeptide containing from about one to about forty amino acids in length. Thus, for example, the term "functional (poly)peptide fragments of CCg", refers to fragments of CCg that retain a CCg activity, e.g., the ability to interact and/or cooperate with a trophic factor such as FGF-2 to stimulate the growth or differentiation of progenitor and/or stem cells, preferably neural progenitor and/or stem cells. One of skill in the art could use the proliferative assay described in the present Examples to identify fragments of CCg that are functional in stimulating proliferation of neural undifferentiated cells in combination with FGF-2. Biologically functional fragments, for example, can vary in size from a polypeptide fragment or as small as an epitope capable of binding an antibody molecule to a large polypeptide capable of participating in the characteristic induction or programming of phenotypic changes within a cell. Several regions of CCg have been identified. An available glycosylation site of CCg is located at amino acid residue 79 in rat cystatin C, or one of the aspartic acid residues in human cystatin C. The protease inhibitor region is located from about amino acid 7 or 8, preceding conserved glycine at residue 9 (in chicken) (Machleidt et al., FEBS Letters, 1989, 243:234–238; Abrahamson, et al., J. Biol. Chem. 1987, 262:9688–9694; Hall et al., J. Biol. Chem., 1995, 270:5115–5121). An example of a functional fragment of CCg includes a fragment containing the glycosylation site, a fragment lacking the protease inhibitor region, and the like.

Functional fragments of CCg may also include inhibitory fragments. For example, fragments of CCg that inhibit neural undifferenetiated cell proliferation can be determined using the proliferation assay described herein. One of skill in the art could use CCg and FGF-2 to stimulate cell proliferation and add varying amounts of different CCg peptides to determine if such peptides or fragments have an antagonistic effect with respect to CCg. Further, non-glycosylated fragments of cystatin C are useful as CCg antagonists and can be assayed in a similar manner.

Invention CCg includes amino acid sequences substantially the same as the sequence encoding the cystatin C, including rat or mouse cystatin C, chicken cystatin C, human cystatin C, and the like. The term "substantially the same" refers to amino acid sequences that retain the activity of CCg as described herein, e.g., stimulation and/or potentiation of neurotrophin activity. The CCg glycoproteins of the invention include conservative variations of the amino acid sequence. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like, so long as the glycosylation site is preserved. The term "conservative variation" also includes the use of a substituted amino acid in place of an unsubstituted parent amino acid provided that antibodies raised to the substituted polypeptide also immunoreact with the unsubstituted polypeptide, and that the glycosylation site is preserved. Those of skill in the art will readily recognize substitution, additions and deletions which can be made in the present invention, including employing programs such as Blast to allow such changes.

Minor modifications of the CCg primary amino acid sequence may result in glycoproteins which have substantially equivalent activity as compared to the unmodified counterpart polypeptide described herein. Such modifications may be deliberate, as by site-directed mutagenesis, or may be spontaneous. All of the glycoproteins produced by these modifications are included herein as long as the biological activity of CCg still exists. Further, deletion of one or more amino acids can also result in a modification of the structure of the resultant molecule without significantly altering its activity. Deletion can lead to the development of a smaller active molecule which could have broader utility. For example, it may be possible to remove amino- or carboxy-terminal amino acids without affecting CCg activity, as long as the glycosylation site is preserved.

In a preferred embodiment of the present invention, glycosylation of CCg, more preferably N-glycosylation, stimulates undifferentiated cells to proliferate. A "glycoprotein" is a polypeptide that contains one or more carbohydrate groups. Glycosylation has been shown to affect protein folding, recognition, and metabolism. Most proteins sequestered in the lumen of the endoplasmic reticulum before being secreted from the cell or transported to other intracellular destinations are glycoproteins, while the soluble proteins of the cytoplasm are generally not glycosylated (see Alberts, B., et al., Molecular Biology of the Cell. Garland Publishing, Inc., New York, 1983, herein incorporated by reference).

The carbohydrate moiety of a glycoprotein can be either single monosaccharides or relatively short oligosaccharide (up to 30) oligosaccharides. The carbohydrate portion of a glycoprotein may constitute from about 1 percent to about 50 percent or more of the glycoprotein. Generally, the carbohydrate is covalently attached to a protein as an oligosaccharide side chain containing 4 to 15 sugars. Several side chains may occur on the same protein and the chains may be branched.

The carbohydrate moiety may be linear or branched, and the carbohydrate linkage can be either an O- or an N-linkage. "N-linked glycosylation" refers an alkali-stable N-glycosidic bond between the amide nitrogen of asparagine and the C-1 of an amino sugar residue. This occurs in the sequence motif of Asn—X—Ser, or Asn—X—Thr, where X can be any amino-acid except proline or asparagine. The first sugar of N-glycans is generally N-Acetylglucosamine (GlcNAc), which is linked to the amide nitrogen of Asn. In general, the N-linked oligosaccharides have a minimum of five sugar residues, and fall into three categories, complex, hybrid, and high-mannose type. All of the types have a common pentasaccharide core, and thus have a minimum of five sugar residues. Complex type chains can be mon-, bi-, tri-(2,4 and 2,6 branched), tetra-, and pentantennary structures. Such chains can also contain different amounts of sialic acid. High mannose oligosaccharides can have from about three to about 60 mannose residues. N-linked glycoproteins often have many glycoforms. A "glycoform" is a glycoprotein that differs in the sequences, locations, and/or number of the covalently bound oligosaccharides.

In contrast to N-linked glycosylation, "O-linked glycosylation" refers to oligosaccharides that are attached to a hydroxyl group of serine or threonine. The first sugar residue is usually N-Acetylgalactosamine (GalNAc). Less commonly, galactose, mannose or xylose form O-glycosidic bonds with serine or threonine. In general, O-linked oligosaccharides are generally short (1–4 sugar residues), however, longer forms have been identified (e.g., in the O-glycans of ABO blood group antigens). The longest O-linked carbohydrate chains have been identified in proteoglycans which can contain up to 1000 disaccharide units.

The carbohydrate moiety can be composed of any one of a number of sugars, such as the aldoses. Examples of aldoses include, but are not limited to: D-glyceraldehyde, D-erythrose, D-threose, D-ribose, D-arabinose, D-xylose, S-lyxose, D-allose, D-altrose, D- glucose, D-mannose, D-gulase, D-idose, D-galactose, and D-talose. The carbohydrate moiety may also be a ketose. Examples of ketoses include, but are not limited to, dihydroxyacetone, D-erythrulose, D-ribulose, D-xylulose, D-fructose, D-sorbose, D-tagatose, and D-paicose. The carbohydrate moiety can be composed of hexoses. In one embodiment, CCg includes at least about fifteen hexose residues. A terminal sialic acid residue can be linked to the terminal hexose residue.

Invention co-factors can be produced using molecular cloning techniques well known to one of skill in the art . For example, a polynucleotide sequence encoding invention polypeptide (see Esnard, F., et al., 1990, *Biol. Chem. Hoppe-Seyler* 371:161–166; Turk, V. and Bode, W., 1991, *FEBS Lett.* 285:213–219, both herein incorporated by reference) can be utilized. The term "polynucleotide" or "nucleic acid sequence" refers to a polymeric form of nucleotides at least 10 bases in length. "Isolated polynucleotide" refers to a polynucleotide that is not immediately contiguous with either of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides can be ribonucleotides, deoxyribonucleotides, or modified forms of either nucleotide. The term includes single and double forms of DNA.

DNA sequences encoding invention co-factors can be expressed (and modified, e.g., glycosylated, in vitro) by DNA transfer into a suitable host cell. Host cells are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Suitable host cells also include eukaryotic cells which can glycosylate invention polypeptides, such as CCg. Suitable host cells also include prokaryotic cells which can produce non-glycosylated CCg or eukaryotic cells which are deficient in one or more glycosylation pathways such that they produce non-glycosylated CCg. Methods of stable transfer, meaning that the foreign DNA is continuously maintained in the host, are known in the art. In the present invention, the invention polynucleotide sequences may be inserted into an expression vector. The term "expression vector" refers to a plasmid, virus or other vehicle known in the art that has been manipulated by insertion or incorporation of the nucleic acid sequences encoding invention polypeptides.

"Transformation" refers to a genetic change induced in a cell following incorporation of new DNA (ie., DNA exogenous to the cell). Where the cell is a mammalian cell, the genetic change is generally achieved by introduction of the DNA into the genome of the cell (i.e., stable). "Transformed cell" refers to a cell into which (or into an ancestor of which) invention polynucleotides have been introduced, by such means as recombinant DNA techniques. Transformation of a host cell with recombinant DNA may be carried out by conventional techniques as are well known to those skilled in the art. For exarnple, when the host is a eukaryote, such methods of transfection of DNA as calcium phosphate co-precipitates, conventional mechanical procedures such as microinjection, electroporation, insertion of a plasmid encased in liposomes, or virus vectors may be used.

Isolation and purification of the expressed invention polypeptides, or fragments thereof, provided by the invention, may be carried out by conventional means including preparative chromatography and immunological separations involving monoclonal or polyclonal antibodies.

Invention polypeptides can be used to produce antibodies which are immunoreactive or bind to epitopes of the invention polypeptide. For example, antibodies can be produced which specifically bind to CCg, a non-glycosylated form of CCg, or a specific fragment of CCg. Antibodies which consist essentially of pooled monoclonal antibodies with different epitopic specificities, as well as distinct monoclonal antibody preparations are included within the scope of the invention.

Polyclonal antibodies can also be used in the method of the invention. The preparation of polyclonal antibodies is well-known to those skilled in the art. See, for example, Green et al., 1992, Production of Polyclonal Antisera, in: *Immunochemical Protocols* pages 1–5, Manson, ed., Humana Press; Coligan et al., 1992, Production of Polyclonal Antisera in Rabbits, Rats, Mice and Hamsters, in: *Current Protocols in Immunology*, section 2.4.1, which are hereby incorporated by reference.

The preparation of additional monoclonal antibodies likewise is conventional. See, for example, Kohler & Milstein, 1975, *Nature* 256:495; Coligan et al., sections 2.5.1–2.6.7; and Harlow et al., in: *Antibodies: a Laboratory Manual*, page 726, Cold Spring Harbor Pub., 1988, which are hereby incorporated by reference. Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan et al., sections 2.7.1–2.7.12 and sections 2.9.1–2.9.3; Barnes etal., 1992, Purification of Immunoglobulin G (IgG), in: *Methods in Molecular Biology*, Vol. 10, pages 79–104, Humana Press.

Methods of in vitro and in vivo multiplication of monoclonal antibodies are well known to those skilled in the art. Multiplication in vitro may be carried out in suitable culture media such as Dulbecco's Modified Eagle Medium or RPMI 1640 medium, optionally supplemented by a mammalian serum such as fetal calf serum or trace elements and growth-sustaining supplements such as normal mouse peritoneal exudate cells, spleen cells, thymocytes or bone marrow macrophages. Production in vitro provides relatively pure antibody preparations and allows scale-up to yield large amounts of the desired antibodies. Large scale hybridoma cultivation can be carried out by homogenous suspension culture in an airlift reactor, in a continuous stirrer reactor, or in immobilized or entrapped cell culture. Multiplication in vivo may be carried out by injecting cell clones into mammals histocompatible with the parent cells, e.g., syngeneic mice, to cause growth of antibody-producing tumors. Optionally, the animals are primed with a hydrocarbon, especially oils such as pristane (tetramethylpentadecane) prior to injection. After one to three weeks, the desired monoclonal antibody is recovered from the body fluid of the animal.

Antibodies of the present invention may also be derived from subhuman primate antibody. General techniques for raising therapeutically useful antibodies in baboons can be found, for example, in Goldenberg et al., 1991, International Patent Publication WO 91/11465, and Losman et al., 1990, Int. J. Cancer 46:310, which are hereby incorporated by reference.

Alternatively, an anti-CCg antibody may be derived from a humanized monoclonal antibody. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., 1989, Proc. Nat'l Acad. Sci. USA 86:3833, which is hereby incorporated in its entirety by reference. Techniques for producing humanized monoclonal antibodies are described, for example, by Jones et al., 1986, Nature 321:522; Riechmann et al., 1988, Nature 332:323; Verhoeyen et al., 1988, Science 239:1534; Carter etal., 1992, Proc. Nat'l Acad. Sci. USA 89:4285; Sandhu, 1992, Crit. Rev. Biotech. 12:437; and Singer et al., 1993, J. Immunol. 150:2844, which are hereby incorporated by reference.

Antibodies of the invention also may be derived from human antibody fragments isolated from a combinatorial immunoglobulin library. See, for example, Barbas et al., 1991, in: Methods: a Companion to Methods in Enzymology, Vol. 2, page 119; Winter etal., 1994, Ann. Rev. Immunol. 12:433, which are hereby incorporated by reference. Cloning and expression vectors that are useful for producing a human immunoglobulin phage library can be obtained, for example, from STRATAGENE Cloning Systems (La Jolla, Calif.).

In addition, antibodies of the present invention may be derived from a human monoclonal antibody. Such antibodies are obtained from transgenic mice that have been engineered to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens, and the mice can be used to produce human antibody-secreting hybridomas. Methods for obtaining human antibodies from transgenic mice are described by Green et al., 1994, Nature Genet. 7:13; Lonberg et al., 1994, Nature 368:856; and Taylor et al., 1994, Int. Immunol. 6:579, which are hereby incorporated by reference.

The term antibody as used in this invention includes intact molecules as well as fragments thereof, such as Fab, $F(ab')_2$, and Fv which are capable of binding the epitopic determinant. These antibody fragments retain some ability to selectively bind with its antigen or receptor and are defined as follows:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) $(Fab')_2$, the fragment of the antibody that can be obtained by treating whole antibody with the enzyme pepsin without subsequent reduction; $F(ab')_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody (SCA), defined as a genetically engineered molecule containing the variable region of the light chain, the variable region of the heavy chain, linked by a suitable polypeptide linker as a genetically fused single chain molecule.

Methods of making these fragments are known in the art. (See for example, Harlow and Lane, 1988, *Antibodies: A Laboratory Manual*, Cold Spring Harbor Laboratory, New York, incorporated herein by reference). As used in this invention, the term epitope means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Antibody fragments of the present invention can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted $F(ab')_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and No. 4,331,647, and references contained therein. These patents are hereby incorporated in their entireties by reference. See also Nisonhoff et al., 1960, Arch. Biochem. Biophys. 89:230; Porter, 1959, Biochem. J. 73:119; Edelman et al., 1967, *Methods in Enzymology*, Vol. 1, page 422, Academic Press; and Coligan et al. at sections 2.8.1–2.8.10 and 2.10.1–2.10.4.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

For example, Fv fragments comprise an association of $V_H$ and $V_L$ chains. This association may be noncovalent, as described in Inbar et al., 1972, *Proc. Nat'l Acad. Sci. USA* 69:2659. Alternatively, the variable chains can be linked by an intermolecular disulfide bond or cross-linked by chemicals such as glutaraldehyde. See, e.g, Sandhu, supra. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow et al., 1991, *Methods: a Companion to Methods in Enzmology*, Vol. 2, page 97; Bird et al., 1988, *Science* 242:423–426; Ladner et al., U.S. Pat. No. 4,946,778; Pack et al., 1993, *Bio/Technology* 11:1271–77; and Sandhu, supra.

Another form of an antibody fragment is a peptide coding for a single complementarity- determining region (CDR). CDR peptides (minimal recognition units ) can be obtained by constructing genes encoding the CDR of an antibody of interest. Such genes are prepared, for example, by using the polymerase chain reaction to synthesize the variable region from RNA of antibody-producing cells. See, for example, Larrick et al., 1991, *Methods: a Companion to Methods in Enzymology*, Vol. 2, page 106.

Antibodies which bind to CCg can be prepared using an intact glycoprotein or fragments containing small glycosylated peptides of interest as the immunizing antigen. The polypeptide or a peptide used to immunize an animal can be derived from translated cDNA or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled glycosylated peptide is then used to immunize the animal (e.g., a mouse, a rat, or a rabbit).

If desired, polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan et al., Unit 9, *Current Protocols in Immunology*, Wiley Interscience, 1991, incorporated by reference).

An in vitro assay system to identify polypeptides involved in the proliferation of cells is also provided. This assay system can be used to identify novel co-factors which stimulate and/or potentiate the activity and/or specificity of trophic factors. According to the present invention, there are provided methods for identifying co-factors for trophic factors, comprising culturing cells in a conditioned media at low density, contacting the cells with a trophic factor and thereafter purifying the co-factor from the conditioned media which stimulates and/or potentiates the trophic factor. Preferably, the co-factor is an autocrine and/or paracrine co-factor which can be identified and purified from the conditioned medium by fractionation or other methods known to those skilled in the art to purify proteins, and/or identify protein-protein interactions.

Established long-term cultures of adult rat hippocampus-derived neural progenitor cells (AHPs) in the presence of FGF-2 (Gage et al. (1995) *Proc. Natl. Acad. Sci. USA*, herein incorporated by reference) are shown herein. It was previously recognized that the culturing of cells in the presence of trophic factors requires a high cell density. For example, FGF-2 has been shown to require a high cell density for culturing AHPs, whereas the expansion of clonal populations of AHPs from single cells with FGF-2 was unsuccessful unless FGF-2 was supplemented with AHP CM. At low cell density, FGF-2 alone does not support neural stem cell proliferation or survival, and elicits a weak mitogenic activity on neural undifferentiated cells, as they do not expand farther than a few cell division. The present discovery identifies that trophic factors, such as FGF-2, require cooperation with co-factors which are present in the conditioned medium. For example, the autocrine/paracrine co-factor(s), CCg, present in the CM, supports neural stem cell and progenitor cell proliferation in vitro. Further, the CM-derived co-factor potentiates the activity of FGF-2 in vivo and therefore cooperates with FGF-2 to induce proliferation of endogenous neural stem cells in the adult brain. The present invention and the Examples provided herein provide an autocrine/paracrine co-factor that cooperates with FGF-2 to stimulate the proliferation of neural stem cells in vitro and neurogenesis in vivo. Furthermore, this discovery permits the formulation of the hypothesis that trophic factors can achieve activity, and therefore specificity, through required interaction with local autocrine or paracrine co-factors.

As used herein, the term "conditioned media" is media contacted with a cell for such an amount of time that the products from the cell are secreted into the media. In one embodiment the cell is a neural undifferentiated cell and preferably, a mammalian cell. Examples include rat, mouse, bovine or ovine cells. Those of skill in the art can readily prepare conditioned medium (CM) for specific cells (see, e.g., Temple, S. (1989) *Nature* 340:471–473; Kilpatrick & Bartlett (1993) *Neuron* 10:255–265; Davis & Temple (1994) *Nature* 372:263–266; Qian et al. (1997) *Neuron* 18:81–93; Johansson et al. (1999) *Cell* 96:25–34, each herein incorporated by reference).

The invention co-factors can be purified by any means known to one of skill in the art. One specific method of purification includes producing conditioned media from mammalian undifferentiated cells, and fractionating the medium to isolate the co-factor. Fractionation can be performed by affinity chromatography on the media and eluting fractions containing mitogenic activity, papain chromatography on the fraction containing mitogenic activity, and the like, as well as combinations of fractionation methods. In a preferred embodiment of the present invention, the conditioned media is subject to affinity chromatography, and fractions containing mitogenic activity are eluted, using methods well known to one of skill in the art. In one embodiment, the affinity is chromatography is lentil-lectin chromatography, and elution is performed with I-methyl-mannoside. Papain chromatography is then performed on the eluted fractions having mitogenic activity. Exemplary methods for purifying CCg are shown in Example 1, using a cation exchange column and Example 4, using lentil lectin chromatography.

As employed herein, the term "low density" refers to the density at which most of the cells would die in the presence of trophic factors alone but would proliferate with trophic factors when supplemented with CM obtained from high density rapidly proliferating cell cultures. See Example 2, wherein the neuronal undifferentiated cells are cultured at a low density in a basal medium. It has been discovered that cells will proliferate in the presence of trophic factors only when in high density, and not at low density unless a co-factor is provided therewith.

In one preferred embodiment, the invention provides a method of identifying an agent which promotes neuronal cell proliferation, by contacting an agent of interest, such as a polypeptide, with the neuronal undifferentiated cells and CCg and measuring the ability of the cells to proliferate by any means known to one of skill in the art. The agent is evaluated to measure its influence on neuronal proliferation, influence on synaptic functions, and/or to promote the survival of neurons. The ability of the neuronal undifferentiated cells to proliferate is then compared to the ability of a suitable control population of cells to proliferate in the absence of the agent. The neural undifferentiated cells can be either adult cells or embryonic cells. The neuronal undifferentiated cells can be derived from either the peripheral or the central nervous system. In one embodiment, the cells are derived from the central nervous system, specifically from the hippocampus (see Ray, J., et al., 1993, *Proc. Natl. Acad. Sci. USA* 90:3602–3606, herein incorporated by reference, also see Example 1). A specific, nonlimiting example of a suitable control population of cells is neuronal undifferentiated cells cultured at low density in basal medium supplemented with FGF-2. The multipotent neural progenitor cells are cultured at "low density". (e.g, DMEM/F12). The basal medium is supplemented with fibroblast growth factor-2 at 0.10–50 ng/ml. In one embodiment, the basal media is supplemented with fibroblast growth factor-2 at about 5–20 ng/ml.

The term "agent", "compound" or "factor" as used herein describes any molecule, e.g., a protein, polypeptide, or pharmaceutical, with the capability of affecting the growth of a neural undifferentiated cell. The agent can be anything known or suspected of being capable of affecting the growth or neuronal undifferentiated cells. The agent includes peptide fragments of CCg polypeptide. The agents include synthetic chemical agents, biochemical agents, cells, extracts, homogenates and conditioned medium. The test agent may also be a combinatorial library for screening a plurality of compounds. Compounds identified in the method of the invention can be further evaluated, detected, cloned, sequenced, and the like, either in solution or after binding to a solid support, by any method usually applied to the detection of a specific DNA sequence, such as PCR, oligomer restriction (Saiki et al., *Bio/Technology* 3:1008–1012, 1985), allele-specific oligonucleotide (ASO) probe analysis (Conner et al., *Proc. Natl. Acad. Sci. USA* 80:278, 1983), oligonucleotide ligation assays (OLAs) (Landegren et al., *Science* 241:1077, 1988), and the like. Molecular techniques for DNA analysis have been reviewed (Landegren et al., *Science* 242:229–237, 1988).

Candidate agents encompass numerous chemical classes. They can be organic molecules, preferably small organic compounds having a molecular weight of more than 50 and less than about 2,500 Daltons. Candidate agents comprise functional groups necessary for structural interaction with proteins, particularly hydrogen bonding, and typically include at least an amino, carbonyl, hydroxyl or carboxyl group, preferably at least two functional chemical groups. The candidate agents often comprise cyclical carbon or heterocyclic structures and/or aromatic or polyaromatic structures substituted with one or more of the above functional groups. Candidate agents are also found among biomolecules including, but not limited to: peptides, saccharides, fatty acids, steroids, purines, pyrimidines, derivatives, structural analogs or combinations thereof. Candidate agents can be polypeptides, or polypeptides produced by site-directed or random mutagenesis of a synthetic or naturally occurring nucleic acid sequence.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

In yet another embodiment of the present invention, there are provided methods for stimulating and/or potentiating trophic factor activity and/or specificity, comprising administering at least one co-factor (or a biologically active fragment thereof), alone or in combination with at least one trophic factor (or a biologically active fragment thereof), to a cell. As used herein, the term "stimulate and/or potentiate" refers to the ability of co-factors to promote, induce, enhance, increase or lengthen trophic factor activity and/or specificity, both in vivo and in vitro. Those of skill in the art will readily recognize the activity and/or specificity of trophic factors. For example, Nerve Growth Factor (NGF), Brain-derived growth factor (BDGF), acidic and basic fibroblast growth factor (aFGF and bFGF, respectively), and Growth Promoting Factors 2 and 4 ($GPF_2$ and $GPF_4$) are factors known to influence neural growth (Gregory R. Bock et al. Growth Factors As Drugs for Neurological and Sensory Disorders (Ciba Foundation Symposium, No 196) (John Wiley & Son Ltd, 1996); Apfel, S. C., Clinical Applications of Neurotrophic Factors (Lippincott Williams & Wilkins, 1997); Shihabuddin et al. Mol Med Today (1999) 5(11):474–80; Svendsen et al. Brain Pathol. (1999) 9(3):499–513, each herein incorporated by reference), as well as other systems (see, e.g., Aloe et al. Microsc Res Tech. (1999) 45(4–5):285–91; Simone et al. Hematol Oncol. (1999) 17(l):1–10, each herein incorporated by reference). Other applications of invention co-factors will be readily recognized based on the applications of trophic factors (see, e.g., Amant et al. Drugs. (1999) 59 Spec No:33–6; Cooper D. M. Nurse Pract Forum. (1999) 10(2):74–86; Malgrange et al. Int J Pediatr Otorhinolaryngol. (1999) 49 Suppl 1:S19–25; Alexis & Sekeris, Activation of Hormone and Growth Factor Receptors: Molecular Mechanisms and Consequences (NATO Asi Series C: Mathematical and Physical Sciences) (Kluwer Academic Publishers, 1990), Wingard & Demetri, Clinical Applications of Cytokines and Growth Factors (Kluwer Academic Publishing, 1999); Woo et al. Clin Orthop. (1999) (367 Suppl):S312–23; Warburton et al. Biochem Cell Biol. (1998) 76(6):971–95; Devlin et al. Can J Cardiol. (1999) 15(6):676–82; Matsuzaki & Yoshizato, Wound Repair Regen (1998) 6(6):524–30, each herein incorporated by reference).

In addition, specific cell type responses also have been associated with particular trophic factors. Epidermal growth factor (EGF) and fibroblast (FGF-2)-growth factors, influence the extent and rate of proliferation of neural stem and progenitor cells in vitro and in vivo (Reynolds & Weiss (1992) *Science* 255:1707–1710; Richards et al. (1992) *Proc.*

*Natl. Acad. Sci. USA* 89:8591–8595; Vescovi et al. (1993) *Neuron* 11:951–966; Gage et al. (1995) *Proc. Natl. Acad. Sci. USA* 92:11879–11883; Kuhn et al. (1997) *J. Neurosci.* 17:5820–5829; Wagner et al. (1999) *J. Neurosci.* 19:6006–6016; Reynolds & Weiss (1996) *Develop. Biol.* 175:1–13; Gritti et al. (1996) *J. Neurosci.* 16:1091–1100). EGF and TGF.alpha. stimulate the proliferation of keratinocytes, TGF.beta. stimulates collagen and fibronectin synthesis, PDGF stimulates angiogenesis and granulation tissue formation and FGF-7 stimulates epithelial cell proliferation (Staiano-Coico et al., J. Exp. Med. (1993) 178:865–878). PDGF, FGF-2 and a recently described heparin binding epidermal growth factor HB-EGF (Higashiyama et. al., Science (1991) 251:936–939) additionally are involved in the proliferation and migration of vascular smooth muscle cells and vascular endothelial cells. Those of skill in the art will readily recognize additional cell type responses associated with each particular trophic factors (see, e.g.,Lenfant et al., (1992); Aebischer et al. (1998); Meager & Robinson, (1999); McKay & Brown, (1998); Leroith & Bondy, (1996), Alexis & Sekeris, (1990). Each of the references are hereby incorporated by reference.

In yet a more preferred embodiment, the present invention is based on the purification and characterization of co-factors from the conditioned medium of neural undifferentiated cell cultures. For example, the co-factor CCg which is required for FGF-2's mitogenic activity on neural undifferentiated stem cells has been purified. Accordingly, there are provided methods for stimulating neurogenesis comprising administering a co-factor, alone or in combination with neurotrophins, to cells in need thereof. In its most preferred embodiment, this co-factor is an autocrine/paracrine co-factor, a glycosylated form of cystatin C (CCg), and whose glycosylation is required for its activity. The process of neurogenesis is controlled by the cooperation between trophic factors and autocrine/paracrine co-factors, of which CCg is a prototype.

In practicing the most preferred embodiment of the present invention, a neural undifferentiated cell is contacted with CCg, or a biologically active fragment thereof, and fibroblast growth factor-2 (FGF-2), or a biologically active fragment thereof. FGF-2 is an 18 kDa protein with a length of 155 amino acids and an isoelectric point of 9.6. FGF-2 does not contain disulfide bonds and is not glycosylated. Shorter variants with a length of 131 and 146 amino acids have been described, as have some higher molecular weight forms (22, 23, 24, 25 kDa). The properties of FGF-2 have been extensively reviewed (e.g, see Baird, A., & Klagsbrun, M., 1991, *Cancer Cells* 3: 239–43; Schweigerer L, "Basic fibroblast growth factor: properties and clinical implications," In: *Growth factors. differentiation factors, and cytokines*, Habenicht A (ed), pp. 42–66, Springer, Berlin, 1990, herein incorporated by reference). The cell can be contacted in vitro or in vivo. This invention includes the combined delivery of FGF-2 and CCg to the adult dentate gyrus to stimulate neurogenesis.

Neurogenesis, first thought to be limited to the prenatal period, occurs throughout adulthood in discrete regions of the brain, i.e., the subventricular zone (SVZ) (Lois & Alvarez-Buylla (1993) *Proc. Natl. Acad. Sci. USA* 90:2074–2077; Luskin, M. B. (1993) *Neuron* 11:173–189, each herein incorporated by reference) and the dentate gyrus (DG) of the hippocampus (Altman & Das (1965) *J. Comp. Neurol.* 124:319–335; Caviness, V. S. (1973) *J. Comp. Neurol.* 151:113–120) of several species, including human (Eriksson et al. (1998) *Nature Medecine* 4:1313–1317, each herein incorporated by reference). During brain development, an excess of neural cells can be produced; wherein the cells migrate toward their target, where a limited supply of trophic factors, produced by the target cells, can regulates their survival (Oppenheim, R. W. (1991)*Ann. Rev. Neurosci.* 14:453–501, each herein incorporated by reference). Neurogenesis is also regulated by a variety of stimuli, which can also be incorporated into the present invention, including steroid hormones (Gould et al. (1992)*J. Neurosci.* 12:3642–3650), aging (Kuhn et al., (1996) *J. Neurosci.* 16:2027–2033), environmental enrichment (Kempermann et al. (1997) *Nature* 386:493–495), genetic background (Kempermann et al. (1997) *Proc. Natl. Acad. Sci. USA* 94:10409–10414), stresses (Gould et al. (1998) *Proc. Natl. Acad. Sci. USA* 95:3168–3171) and running (Van Praag et al. (1999) *Nature Neurosci.* 2:266–270); each of these references which are herein incorporated by reference. The process of "neurogenesis" as used herein includes proliferation, migration, survival and differentiation into postmitotic neurons of the putative multipotent neural undifferentiated cells. Neurogenesis also refers to regeneration as well as apoptosis of cells.

As used herein, the term "undifferentiated cell" refers to cells which have the ability to differentiate, including stem cells and progenitor cells. In contrast to undifferentiated cells, differentiated cells have a clearly defined morphology which identifies it as a member of a defined histological type. The cell can be a mammalian cell. In one embodiment, the mammalian cell is a rodent cell. In another embodiment, the cell is a primate cell, such as a human cell.

As used herein, the term "stem cell" refers to the founder cell of embryonic or other cell lineage, which are undifferentiated cells displaying high proliferative potential, generating a wide variety of differentiated progeny including the principal phenotypes of the tissue, possessing the capacity for self-renewal and retaining their multilineage potential over time (Gage et al. (1995) *Annu. Rev. Neurosci.* 18:159–192, each herein incorporated by reference). Stem cells are capable of dividing to produce two daughter cell types with different fates: one is another stem cell identical to the mother cell, and the other is a lineage progenitor cell which will divide to produce more differentiated cells. In adult mammals, stem cells occur in most tissue systems, for example, the bone marrow gives rise to all blood cells and muscle.

As used herein, the term "progenitor cell" refers to undifferentiated cells whose lineal descendants differentiate along the appropriate pathway to produce a fully differentiated phenotype. All differentiated cells have, by definition, a progenitor cell type. For example, neural progenitor cells such as neuroblasts are progenitors for neurons and germ cells for gamete cells. In addition, it is readily recognized that progenitor cells do not differentiate into one type of cell, e.g., neural progenitor cells can give rise primarily to neurons, however, such cells can also rise to astrocytes, glial cells and oligodendrocytes. Those of skill in the art will readily recognize the associated progenitor cells for differentiated cells.

Those of skill in the art will readily recognize the activity of co-factors, based on the activity of trophic factors. For example, "proliferation" means an increase in cell number as a result cell division. Proliferation can be measured by any means known to one of skill in the art. For example, proliferation can be measured by monitoring an increase in cell number, by measuring the uptake of $^3$H-thymidine, by measuring the DNA content of cells, by measuring cellular density, and the like. Incubating includes conditions which allow contact between CCg and the neural undifferentiated cell. Exemplary culture medium is basal media (e.g., HAM/ F12) supplemented with N2 and glutamine. Contacting includes in solution and solid phase. "Differentiation" is the process of acquiring individual characteristics that occurs during the progressive diversification of cells and tissues. Differentiation can be measured by a number of assays known to one of skill in the art. Specific, nonlimiting examples, of assays to measure differentiation include an assessment of the expression of neural or glial specific antigen, an analysis of the expression of neurotransmitters, or the experiments which determine ability of a cell to respond to or release neurotransmitters. "Survival" refers to the ability of cells to remain viable for longer periods of time than normal, and can be measured by methods known to those skilled in the art, including measuring cell density, measuring cellular content, and the like. "Migration" refers to the motility of cells. Migration can be determined by measuring intracellular movement, cell shape changes and the movement of portions of the cell, as well as the movements of cells from one place to another.

In accordance with another embodiment of the present invention, there are provided methods of enhancing neurite outgrowth, neuronal survival and neuronal proliferation in a mammalian cell, said method comprising administering to said cell an effective amount of a composition as described herein.

The present invention identifies a co-factor for a trophic factor. More specifically, the present method is directed to administration of CCg, a glycoprotein which promotes the proliferation of neuronal undifferentiated cells and can be used to treat neuronal disorders, alone or in conjunction with a neurotrophic factor such as FGF, more specifically, FGF-2. A "neuronal disorder" or neural disorder is any disorder which involves the nervous system. One type of neuronal disorders is a neurodegenerative disorder. Neurodegenerative disorders include but are not limited to: (1) diseases of central motor systems including degenerative conditions affecting the basal ganglia (e.g., Huntington's disease, Wilson's disease, Striatonigral degeneration, corticobasal ganglionic degeneration, Tourettes syndrome, Parkinson's disease, progressive supranuclear palsy, progressive bulbar palsy, familial spastic paraplegia, spinomuscular atrophy, ALS and variants thereof, dentatorubral atrophy, olivopontocerebellar atrophy, paraneoplastic cerebellar degeneration, cerebral angiopathy (both hereditary and sporadic)); (2) diseases affecting sensory neurons (e.g., Friedreich's ataxia, diabetes, peripheral neuropathy, retinal neuronal degeneration); (3) diseases of limbic and cortical systems (e.g., s cerebral amyloidosis, Pick's atrophy, Retts syndrome; (4) neurodegenerative pathologies involving multiple neuronal systems and/or brainstem (e.g., Alzheimer's disease, AIDS-related dementia, Leigh's disease, diffuse Lewy body disease, epilepsy, Multiple system atrophy, Guillain-Barre syndrome, lysosomal storage disorders such as lipofuscinosis, late-degenerative stages of Down's syndrome, Alper's disease, vertigo as result of CNS degeneration; (5) pathologies arising with aging and chronic alcohol or drug abuse (e.g., with alcoholism the degeneration of neurons in locus coeruleus, cerebellum, cholinergic basal forebrain; with aging degeneration of cerebellar neurons and conical neurons leading to cognitive and motor impairments; and with chronic amphetamine abuse degeneration of basal ganglia neurons leading to motor impairments; and (6) pathological changes resulting from focal trauma such as stroke, focal ischemia, vascular insufficiency, hypoxic-ischemic encephalopathy, hyperglycemia, hypoglycemia or direct trauma.

Subjective symptoms of neurodegenerative disorders include pain, change in sensation including decreased sensation, muscle weakness, coordination problems, imbalance, neurasthenia, malaise, decreased reaction times, tremors, confusion, poor memory, uncontrollable movement, lack of affect, obsessive/compulsive behavior, aphasia, agnosia, visual neglect, etc. Frequently, objective signs, or signs observable by the physician or the health care provider, overlap with subjective signs. Examples include the physician's observation of signs such as decreased reaction time, muscle fasciculations, tremors, rigidity, spasticity, muscle weakness, poor coordination, disorientation, dysphasia, dysarthria, and imbalance. Additionally, objective signs can include laboratory parameters, such as the assessment of neural tissue loss and function by Positron Emission Tomography (PET) or fuictional Magnetic Resonance Imaging MRI), blood tests, biopsies and electrical studies such as electromyographic data.

Therapeutic benefit includes any of a number of subjective or objective factors indicating a response of the condition being treated. This includes measures of increased neural or neuronal proliferation or more normal function of surviving brain areas. In addition, macroscopic methods of evaluating the effects of the invention can be used which may be invasive or noninvasive. Further examples of evidence of a therapeutic benefit include clinical evaluations of cognitive finctions including object identification, increased performance speed of defined tasks as compared to pretreatment performance speeds, and nerve conduction velocity studies.

In yet another preferred embodiment of the present invention, there are provided methods for modulating FGF mediated processes, such method comprising administering to a subject or cell, a composition comprising an invention co-factor, specifically, CCg. FGF has been acknowledged to be associated with angiogenesis (Rosenkranz et al., Med Klin (1999) 94(9):496–504; Malone et al. Int J Biol Markers. (1999)14(1):3–7.), inflammatory bowel diseases (Beck & Podolsky, Inflamm Bowel Dis (1999) 5(1):44–60), strokes (Ay et al., Cerebrovasc Dis (1999) 9(3):131–5), baldness (Matsuzaki et al. Wound Repair Regen. (1998)6(6):524–30), cancers (Szabi & Sandor, Eur J Surg Suppl (1998)(582) :99–103), and the like (each of these references are herein incorporated by reference). Those of skill in the art will readily recognize additional FGF mediated processes which can be affected by the present invention.

This invention involves administering to a subject a therapeutically effective dose of a pharmaceutical composition containing the CCg polypeptide or CCg peptide fragment of the present invention and a pharmaceutically acceptable carrier. Administering the pharmaceutical composition of the present invention may be accomplished by any means known to the skilled artisan. By subject is meant any mammal, preferably a human.

The pharmaceutical compositions are preferably prepared and administered in dose units. Solid dose units are tablets, capsules and suppositories. For treatment of a patient, depending on activity of the compound, manner of administration, nature and severity of the disorder, age and body weight of the patient, different daily doses are necessary. Under certain circumstances, however, higher or lower daily doses may be appropriate. The administration of the daily dose can be carried out both by single administration in the form of an individual dose unit or else several smaller dose units and also by multiple administration of subdivided doses at specific intervals.

The pharmaceutical compositions according to the invention are in general administered topically, intravenously, intracerebrally, orally or parenterally or as implants, but even rectal use is possible in principle. Suitable solid or liquid pharmaceutical preparation forms are, for example, granules, powders, tablets, coated tablets, (micro)capsules, suppositories, syrups, emulsions, suspensions, creams, aerosols, drops or injectable solution in ampule form and also preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of present methods for drug delivery, see Langer, 1990, *Science* 249:1527–1533, which is incorporated herein by reference.

The pharmaceutical compositions according to the invention may be administered locally or systemically. By therapeutically effective dose is meant the quantity of a compound according to the invention necessary to prevent, to cure or at least partially arrest the symptoms of the disorder and its complications. Amounts effective for this use will, of course, depend on the severity of the disease and the weight and general state of the patient. Typically, dosages used in vitro may provide useful guidance in the amounts useful for in situ administration of the pharmaceutical composition, and animal models may be used to determine effective dosages for treatment of particular disorders. Various considerations are described, e.g., in Gilman et al., eds., *Goodman And Gilman's: The Pharmacological Bases of Therapeutics*, 8th ed., Pergamon Press, 1990; and *Remington's Pharmaceutical Sciences*, 17th ed., Mack Publishing Co., Easton, Pa., 1990, each of which is herein incorporated by reference.

In yet another embodiment of the present invention, there are provided methods for inhibiting the activity of trophic factors, comprising administering an inactivated co-factor to a cell. It has been discovered, in the present invention, that aco-factors for trophic factors can be activated or inactivated, i.e., able to stimulate and/or potentiate trophic factor activity and/or specificity, or alternatively, inhibit trophic factor activity and/or specificity, respectively. In a preferred embodiment, the present invention provides a method for inhibiting FGF mediated processes (e.g., proliferation of a mammalian neuronal cells, angiogenisis, and the like) by contacting the cell with a non-glycosylated form of stem cell glycocystatin C (CCg) (an inactivate co-factor), or a peptide fragment thereof, under conditions that inhibit proliferation of the cell. The term "inhibit" or "inhibiting" refers to a measurable reduction in activity. A low degree of inhibition refers to a reduction of at least 10% or less versus control, whereas a moderate degree of inhibition refers to a reduction of 50% or more, and a high degree of inhibition refers to a reduction of 80% or more. A "non-glycosylated form" of CCg is a protein with essentially the same amino acid sequence as CCg (e.g., a conservative variation of CCg) that does not have a carbohydrate moiety attached to the amino acid sequence.

In one embodiment, a neuronal undifferentiated cell is contacted with a peptide fragment of non-glycosylated CCg, under conditions such that proliferation is inhibited. A specific, nonlimiting example of non-glycosylated CCg is a peptide fragment of CCg that has the carbohydrate moiety removed. Deglycosylation can be accomplished by removal of the glycosylation sites. For example, this can be done by removing amino acids (e.g., by deletion), by mutation of the glycosylation site, such that one amino acid is substituted for another amino acid, or by substitution of the glycosylation site. A specific, non-limiting example of non-glycosylated CCg is a molecule having a modified glycosylation site that precludes attachment of a carbohydrate moiety. A further specific, non-limiting example is a non-glycosylated fragment of CCg is a non-glycosylated fragment wherein the protease inhibitor has been removed. Another specific, non-limiting example of a non-glycosylated CCg is CCg isolated from a mutant cell, wherein the cell is deficient in its ability to glycosylate polypeptides. Alternatively, the glycosylation can be affected by the use of PNGase-F, wherein the sequence of CCg is intact but the sugar has been removed.

In another embodiment, a method of identifying a peptide which inhibits neuronal progenitor or stem cell proliferation is provided. In one embodiment, the peptide is a peptide fragment of CCg. In another embodiment, the peptide is CCg with a glycosylation site mutated or deleted. In yet another embodiment, the peptide is non-glycosylated CCg. The method includes contacting a neuronal undifferentiated cell with a peptide fragment of non-glycosylated stem cell glycocystatin C and with stem cell glycocystatin C and measuring the ability of the neuronal progenitor or stem cell to proliferate in the presence of the peptide fragment. Proliferation can be measured by any means known to one of skill in the art, as described above. The ability of the neuronal cell contacted with the peptide fragment of non-glycosylated cystatin C is then compared with a the ability of a suitable control cell to proliferate. One such control is a neuronal undifferentiated cell, contacted with CCg, but not contacted with the peptide fragment of non-glycosylated stem cell cystatin C. A decrease in the proliferation of neuronal undifferentiated cells, in the presence or absence of a trophic factor (FGF-2), when contacted with the peptide fragment of non-glycosylated stem cell cystatin C and CCg, as compared to the ability of the neuronal undifferentiated cell contacted with CCg, indicates that the peptide fragment is an antagonist of CCg.

The above disclosure generally describes the present invention. A more complete understanding can be obtained by reference to the following specific examples which are provided herein for purposes of illustration only and are not intended to limit the scope of the invention.

EXAMPLES

Without further elaboration, it is believed that one skilled in the art can, using the preceding description, utilize the present invention to its fullest extent. The following examples are intended to illustrate but not to limit the invention in any manner, shape, or form, either explicitly or implicitly. While they are typical of those that might be used, other procedures, methodologies, or techniques known to those skilled in the art may alternatively be used.

Example 1

In vitro Proliferation Assay

To demonstrate the requirement of an autocrine/paracrine co-factor to support the mitogenic activity of FGF-2, adult rat hippocampus-derived neural progenitor cells (AHPs) were plated at densities at which the cells would die in the presence of FGF-2 alone but would proliferate with FGF-2 when supplemented by AHP conditioned medium (CM) (FIG. 1a). AHPs were cultured as described (Gage et al. (1995) *Proc. Natl. Acad. Sci. USA*). The CM was prepared by incubating 60% confluent cells (passage 17 to 30) for 48 h in DMEM/F12, supplemented with 2.5 mM L-glutamine and N2 supplement (N2 medium) containing FGF-2 (20 ng/ml; recombinant human FGF-2; gift from A. Baird). The medium was replaced and conditioned for 2 more days. The CM was kept at −80° C. until use.

Cell proliferation was monitored in 96-well plates by counting cells at DIV 1 and DIV 5 under a phase contrast microscope (×10). In such a proliferation assay, a net increase, or decrease, in cell number is the result of both cell proliferation and cell survival. DAPI (4', 6-diamidino-2-phenylindole) staining was performed on AHPs plated at low density, and cells in metaphasis were observed, confirming that cell division occured. Cells were examined 4 h after plating and wells containing clusters of >1 cell were omitted from the experiments. For differentiation experiments, cells were cultured in N2 medium containing all-trans RA (1μM, Sigma), FGF-2 (2 ng/ml) and FBS (0.5%, Hyclone) for 10 days (Palmer et al. (1997)). Time-lapse imaging was performed on a chamber mounted on an inverted microscope (Nikon TE300) with a SPOT camera.

Figure 1B:
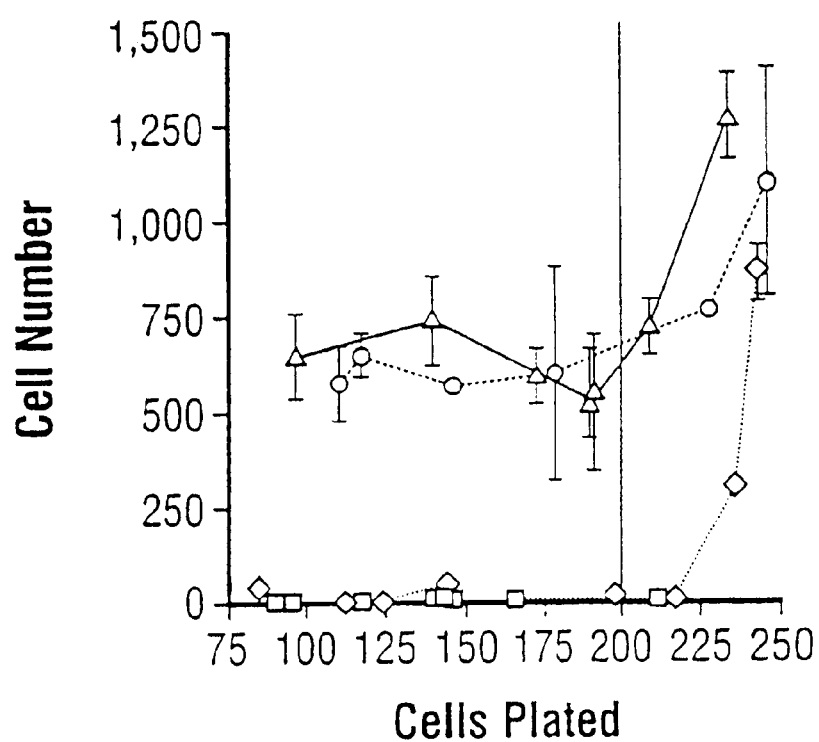

FGF-2 supported the proliferation of AHPs when plated at densities >200 cells per well (0.32 cm$^2$ surface area, FIG. 1b). At lower densities (1 to 200 cells per well), cells cultured with FGF-2 alone died by 5 days in vitro (DIV 5), whereas CM or CM containing FGF-2 (CM+FGF-2) supported their proliferation (FIG. 1b). Thus, the mitogenic activity of FGF-2 is cell density dependent, with high-density cultures producing sufficient amounts of a co-factor(s) to support FGF-2's mitogenic activity, whereas in low-density cultures, an insufficient amount of co-factor is present to cooperate with any levels of FGF-2 to support cell proliferation. The observed mitogenic activity of the CM in the absence of FGF-2 is likely due to the fact that an adequate concentration of FGF-2 added for culturing is still present. Different trophic factors/cytokines, including EGF, tested alone or in combinations, with or without FGF-2, failed to mimic the activity of the CM (Table 1). Statistical analysis by one-way ANOVA showed that there was no difference between groups at DIV 1 (F (3,30) =0.83, p>0.5). At DIV 5, one-way ANOVA showed a significant effect due to treatments (F (3,30)=27.34, p<0.0001). Specific comparisons showed significant differences between all groups p<0.0006), except between N2 and FGF-2 or CM and CM+FGF-2. Comparisons made above and below 200 cells per well showed a significant difference for FGF-2 (t (9)= 2.66, p<0.026) and CM (t (4)=3.17, p<0.034).

Example 2

Purification and Characterization of the Co-Factor

Ten liters of CM were applied to lentil-lectin Sepharose 4B (25 ml, Sigma) equilibrated with 25 mM hepes, pH 7.0, 1 mM MnCl$_2$ and 1 mM CaCl$_2$ and the column was washed with 25 mM hepes, pH 6.5 and 50 mM NaCl. No mitogenic activity was detected in the flow-through. The column was eluted with 250 mM α-methyl-mannoside. The eluent—with the mitogenic activity—was collected, concentrated (Biomax-5, Millipore) and applied to a strongly acidic cation exchanger column (1 ml, Hi-TrapSP, Pharmacia). The non-adsorbing effluent containing the mitogenic activity was collected, concentrated, and resolved on a 15% SDS-PAGE under non-reducing conditions and the proteins were transferred to an Immobilon PVDF membrane (Millipore) (Hames, B. D.). For activity determination, proteins were recovered as follows: after lentil-lectin and cation exchange chromatographies, 2 ml samples were collected, dialyzed (3,000 MWCO) against tissue culture medium and filtered (0.22 μm). After blotting, the membrane was cut into 20 equal fractions and proteins were eluted (Montalero, R. C. (1987) Electrophoresis 8:432–438, each herein incorporated by reference). Since the co-factor of FGF-2 was identified as cystatin C and cystatin C binds to papain with high affinity (Machleidt et al. (1989)), the 21 kDa protein was subsequently purified by a modified protocol consisting of lentil-lectin affinity chromatography followed by papain chromatography (Barret, A. J. (1981) Methods enzymol. 80:771–778 each herein incorporated by reference). CCg protein was purified to near homogeneity as shown by SDS-PAGE and confnmed by HPLC analysis.

Figure 1C:
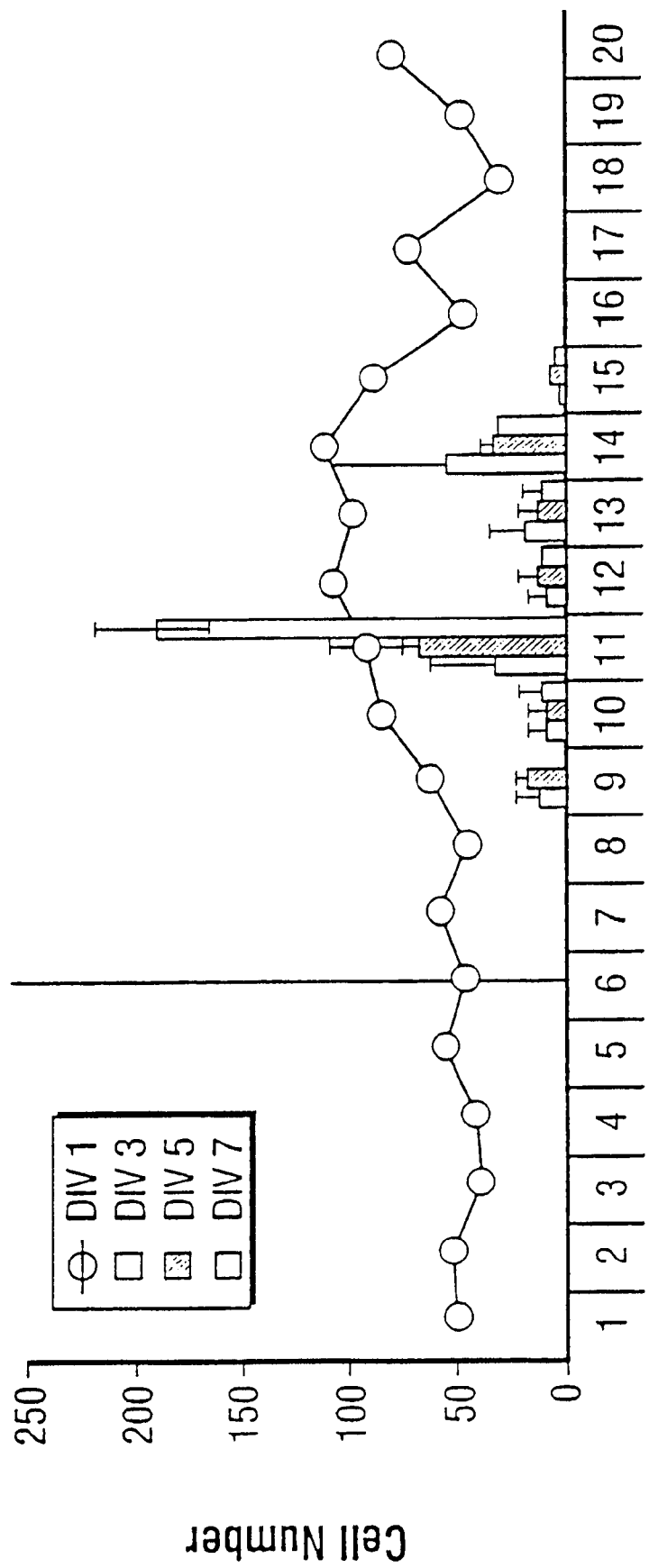

The co-factor purified from the CM and analyzed by SDS-PAGE showed that a 21 kDa protein exhibited most of the activity in the in vitro proliferation assay (FIG. 1c, fraction 11). N-terminal sequencing of the protein yielded a sequence signal of low intensity (GXSXXXXXLLGAXQXADA) (SEQ ID NO:1) that matched the N-terminal sequence of rat cystatin C (Esnard et al. (1990) Biol. Chem. Hoppe-Seyler 371:161–166, each herein incorporated by reference). The identity of the 21 kDa protein was further confirmed by amino acid sequencing and mass spectral analysis of the tryptic peptide fragments. The protein band at 21 kDa was excised and 250 pmoles were subjected to in situ digestion with trypsin. The digested peptides were separated by reverse phase HPLC. The resolved peaks were submitted to sequencing and mass spectral analysis. Peptide G1751 digested with endoproteinase Asp-N was separated by HPLC and analyzed by sequencing and mass spectral analysis. Sequencing was performed on Perkin-Elmer/Applied Biosystems protein sequencer (models 470A and 494) (Fischer et al. (1991) Methods Neurosci. 6:69–84, herein incorporated by reference). All sequences obtained were subjected to a BLAST computer homology search (Altschul et al. (1990) J. Mol. Biol. 215:403–410, herein incorporated by reference). Major fractions were analyzed by matrix assisted laser desorption mass spectroscopy on a Bruker Reflex time-of-flight instrument.

Figure 2B:
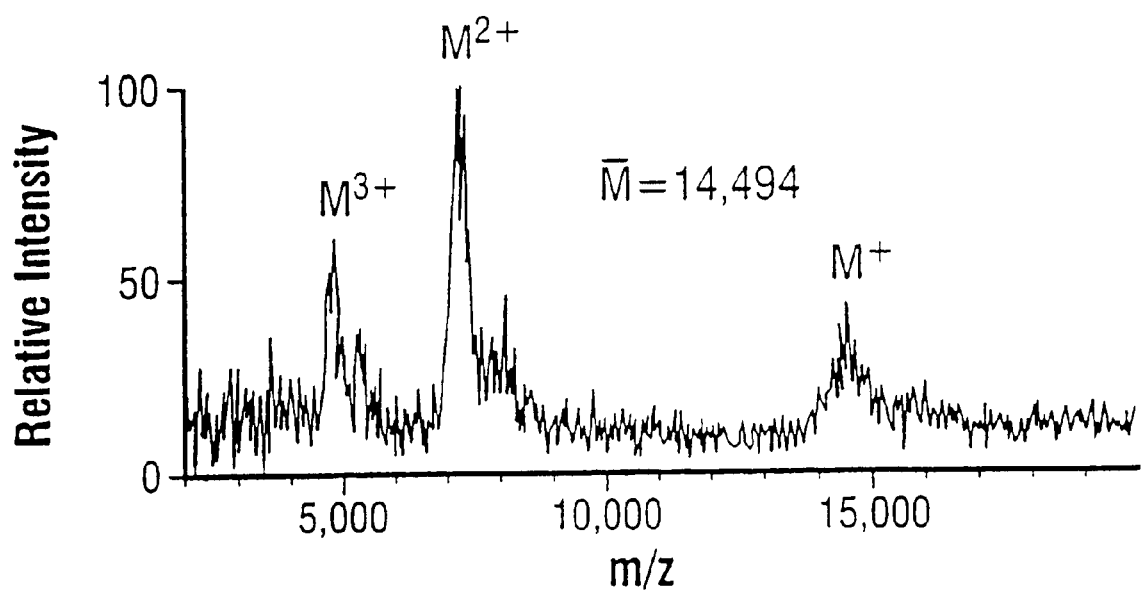
Figure 2C:
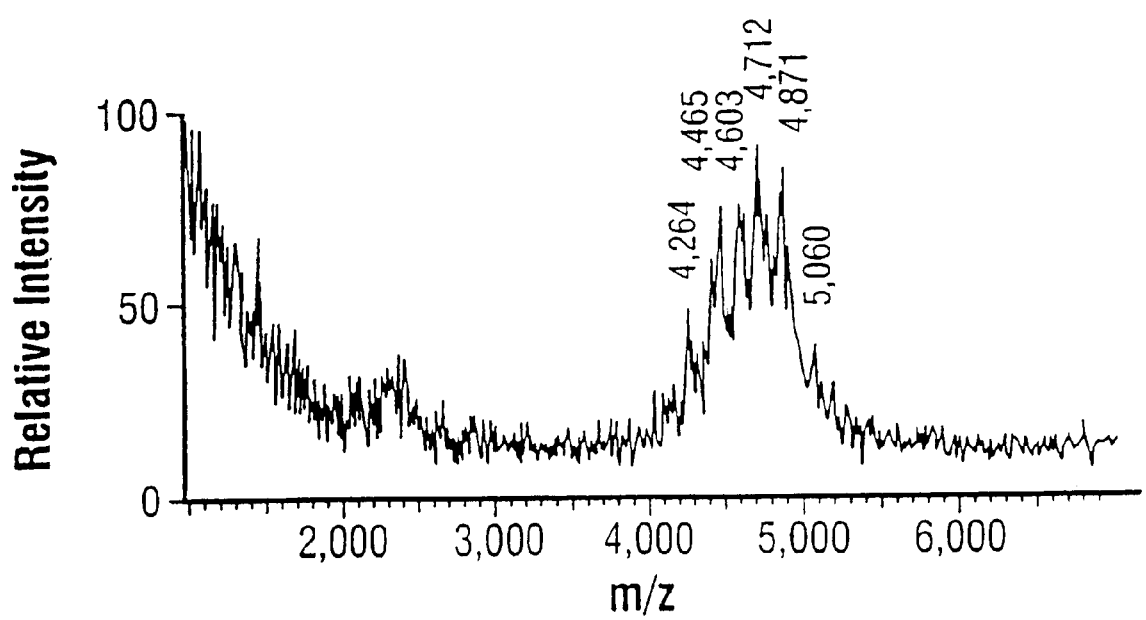

All of the determined sequences (FIG. 2a; 84% of the 21 kDa protein was sequenced) matched rat cystatin C (Esnard et al. (1990) Biol. Chem. Hoppe-Seyler 371:161–166, each herein incorporated by reference). Two peptides, G1752 and G1751, were identified as full length and N-terminally truncated rat cystatin C, respectively. The 21 kDa protein and the peptide G1751 were digested with trypsin and endoproteinase Asp-N, respectively. The peptides, separated by HPLC, were submitted to chemical sequence and mass spectral analysis. Peptide G1754 contained a consensus site for N-glycosylation, carrying a N-linked carbohydrate moiety. The discrepancy between the experimental mass and the theoretical mass calculated from the backbones for the peptides G1750, G1751, G1752 and G1754 indicated that they were indeed glycosylated (FIG. 2a). Furthermore, the mass spectroscopic patterns of the peptides G1751 (FIG. 2b) and G1754 (FIG. 2c) were characteristic of N-glycosylated peptides, indicating that the 21 kDa protein is a glycosylated from of cystatin C (CCg). The deduced mass of the N-linked carbohydrate moiety is approximately 2.4 kDa, corresponding to 15 hexose residues. A carbohydrate moiety of 0.3 kDa is present at the O-glycosylation site (peptide G1750). The molecular weight of 21 kDa as estimated by SDS-PAGE was higher than the value obtained by mass spectral analysis (16 kDa, G1752, FIG. 2a). This discrepancy may be due to the basic nature of the protein and the presence of covalently bound carbohydrates (B. D. Hames, Gel electrophoresis of proteins-A practical approach (B. D. Hames & D. Rickwood, Oxford-Washington D.C.)).

Example 3

N-Glycosylation is Essential for CCg's Activity

Figure 3A:
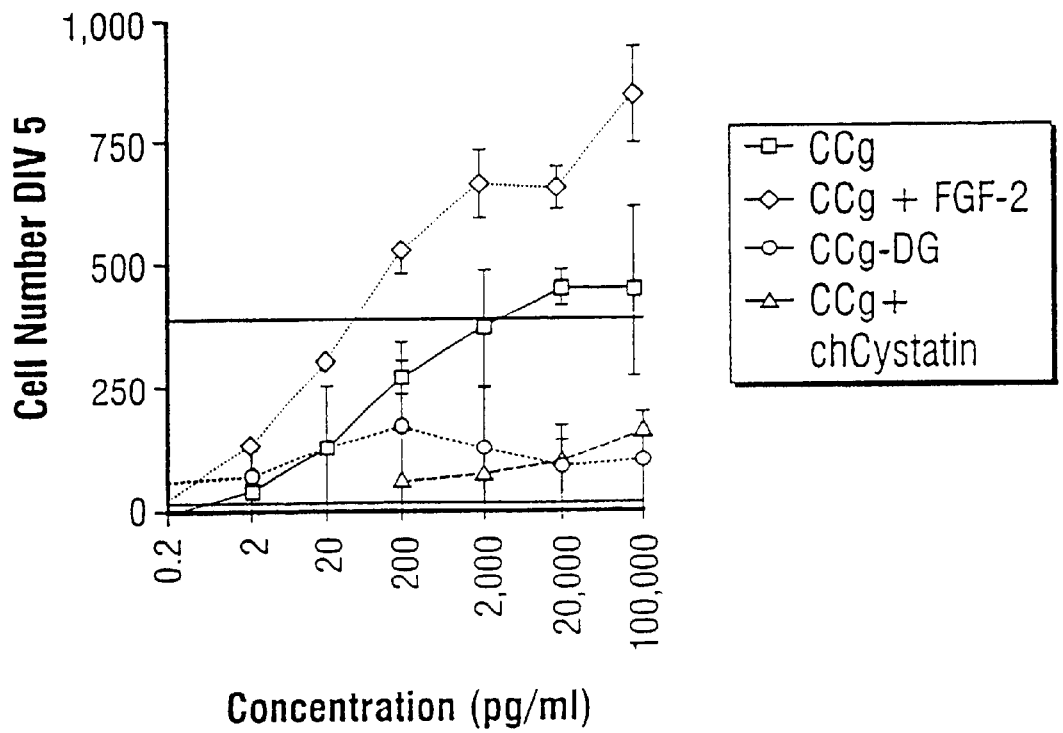
FIGS. 3A–3D are graphs illustrating that the 21 kDa protein (CCg) induces the proliferation of AHPs plated at low density, but not when N-deglycosylated. (A). ChCystatin did not induce the proliferation of AHPs in the absence or presence of FGF-2, but inhibited cell proliferation induced by CM or CM+FGF-2 (B). Three recombinant forms of the mice glycocystatin—wild type (i+g+), a form lacking the protease inhibitory site (i–g+) and a form with mutated N-glycosylation site (i+g–)—were engineered (C) and purified to homogeneity. In (C), NLT is the consensus site for N-glycosylation, DLT is the mutated site where Asn has been subsituted for an Asp; an His tag was fused in 3' to the recombinant sequences. Only the forms i+g+and i–g+, but not i+g–, induced the proliferation in the presence of FGF-2 (D). The average number of cells plated at DIV 1 was below 150 cells per well in (A) and (B) and below 25 cells per well in (D). Data in (A) and (D) are the means of triplicate from one of 3 typical experiments and in (B) are means ±s.e.m. of 3 independent experiments.

Cystatin C, a cysteine proteinase inhibitor (Turk & Bode (1991) *FEBS lett.* 285:213–219, each herein incorporated by reference), is a molecule with pleiotropic functions, with specific domains of the molecule involved in specific functions (Machleidt et al. (1989) *FEBS lett.* 243:234–238; Leung-Tack et al. (1990) *Exp. Cell Res.* 188:16–22, each herein incorporated by reference). It is expressed in the brain (Yasuhara at al. (1993) *Brain Res.* 628:85–92, each herein incorporated by reference), where it is associated with cerebral pathologies such as cerebrovascular amyloidosis (Turk & Bode (1991)). Rat cystatin C is a 13–14 kDa basic protein (Turk & Bode (1991)) containing unique consensus sites for N- (Asn79-X-Thr) and O-glycosylation (Ser3) (Esnard et al. (1990) *Biol. Chem. Hoppe-Seyler* 371:161–166, each herein incorporated by reference). The existence of a glycosylated form of cystatin C has been reported in rat seminal vesicles (Esnard et al. (1988) *Biol. Chem. Hoppe-Seyler* 369:219–222, each herein incorporated by reference). However, the type(s) of glycosylation, N-linked and/or O-linked, and their functional relevance have not been investigated. In the in vitro proliferation assay, CCg at concentrations between 0.02 and 2 ng/ml induced cell proliferation in a dose-dependent manner and was potentiated by FGF-2 (FIG. 3a).

Figure 3B:
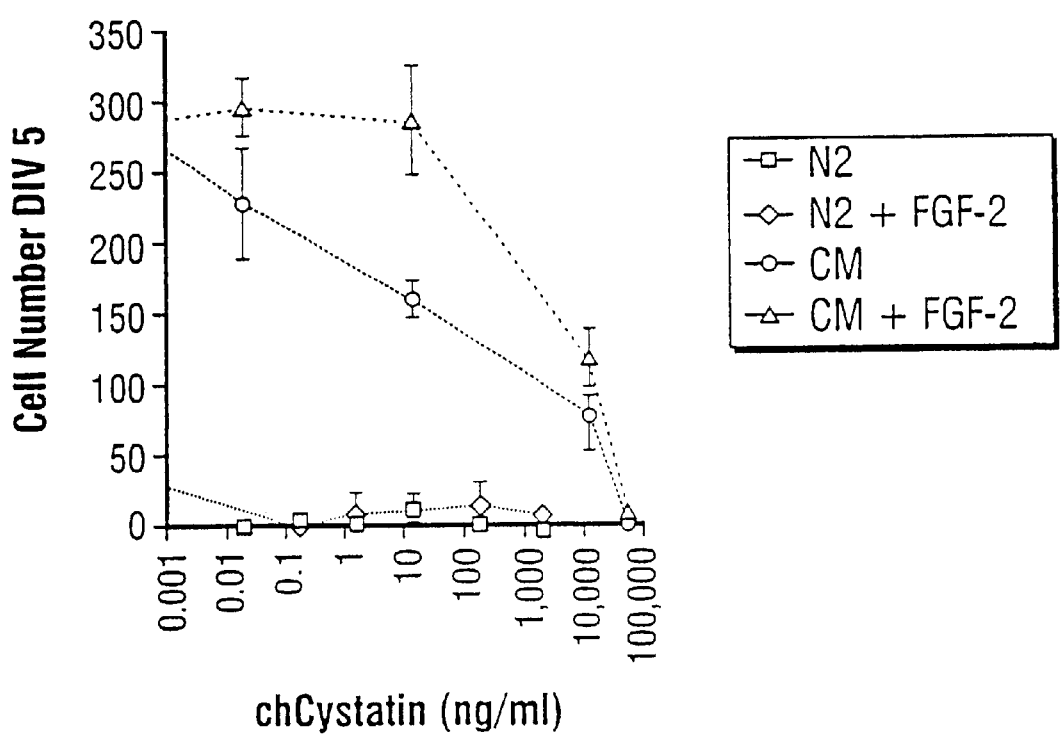

To investigate the importance of the N-linked carbohydrate moiety, CCg was treated with PNGase F, an amidase that removes N-linked oligosaccharides from glycoproteins by cleaving the N-glycosidic bond between Asn and the first hexoseamine. On SDS-PAGE the N-deglycosylated CCg (CCg-DG) exhibited a shift in molecular weight to 19 kDa and appeared sharper than the 21 kDa band, which migrated as a diffuse band due to the presence of the carbohydrates (Keinanen, K.P. (1988) *Biochem. J.* 256:719–724, each herein incorporated by reference). CCg but not the N-deglycosylated form, CCg-DG, induced proliferation; FGF-2 (20 ng/ml) potentiated the activity of Ccg. CCg-DG exhibited no mitogenic activity (FIG. 3a). The importance of glycosylation of CCg is underscored by the fact that chicken cystatin (chcystatin, 1 $\mu$g/ml), which is structurally related to rat cystatin C but lacks the N-glycosylation consensus sequence and thus is not glycosylated (Turk & Bode (1991)), had no activity (FIG. 3b). In fact, it competitively inhibited the mitogenic activity of CCg (FIG. 3a) (Sairam, M. R. (1989) *FASEB J.* 3:1915–1926, each herein incorporated by reference) and of the CM (FIG. 3b). ChCystatin did not induce the proliferation of AHPs in the absence or presence of FGF-2, but inhibited cell proliferation induced by CM or CM+FGF-2. In addition, neither the purified peptide of 22 amino acid length containing the N-carbohydrate moiety (peptide G1754) nor the N-glycosidic chain elicited any activity in the in vitro proliferation assay. The recovery of 100% of the CM activity with CCg, together with the inhibition of the CM activity by the non-glycosylated form of cystatin, indicate that the activity in the CM may be accounted for by CCg.

Figure 3C:
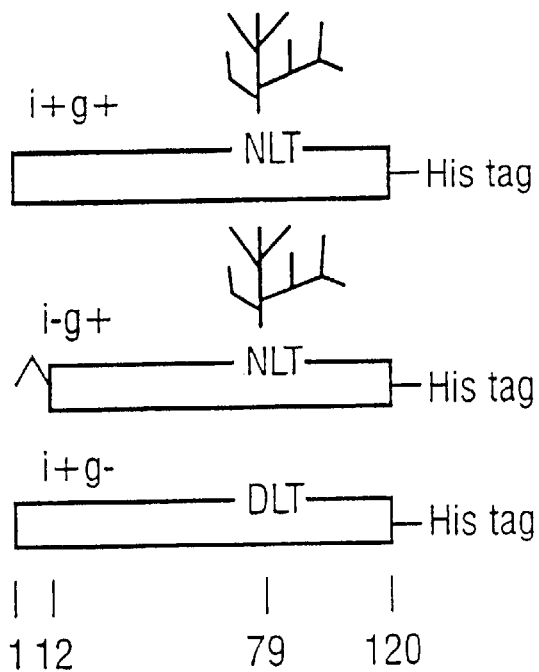

To further investigate the importance of N-glycosylation versus the protease inhibitory domains for the activity of CCg, 3 recombinant forms of the mouse glycocystatin C were engineered (FIG. 3c): 1) a wild type form (i+g+); 2) a mutant form (i-g+), in which the protease inhibitory site was deleted by truncating the 11 N-terminal amino acids, and 3) a second mutant form where the N-glycosylation site was mutated by substituting Asn (79) for Asp (i+g-). Three recombinant forms of CCg were engineered by PCR amplification from a plasmid encoding mouse cystatin C (ATCC 63113): a wild type (i+g+), a mutant lacking the protease inhibitory site (i-g+) and a mutant with a mutated N-glycosylation site (i+g-). To create the mutant forms, sequential PCR amplifications using primers with compatible extensions to introduce base changes were used. Sets of primers were paired appropriately to result in each construct. For i+g+: primer A (SEQ ID NO:10): 5' GAGAGAGAAT-TCATGGCCAGCCCGCTGCGCTCC and B (SEQ ID NO:11): 5' AGAGAGATCGATGGCATTTTTGCAGCT-GAAATTT. For i-g+: primer A, B, C (SEQ ID NO:12) 5' GTCCTGGGCGTGGCCTGGGCGGCCCCG-GAGGAGGCAGATGCC and D (SEQ ID NO:13) 5' CGC-CCAGGCCACGCCCAGGAC. For i+g-: primer A, B, E (SEQ ID NO:14) 5' CGAACTACATGTACCAAGTCCCA-GACAGATTTGACTGACTGT and F (SEQ ID NO:15) 5' GGACTTGGTACATGTAGTTCG. Each variant was fuirther mutated to add an in-frame histidine (His)-tag at the C terminus. As a result of the cloning procedure, 2 differences in the nucleotide sequence of mouse cystatin C were observed: the G in position 71 was found to be a C, and the T in position 276 was found to be a G, when compared to the published sequence (Solem et al. (1990) *Biochem. Biophys. Res. Commun.* 172:945–95, herein incorporated by reference). These nucleotide changes resulted in amino acid substitution of Gly (-5) to Ala and Phe (64) to Leu. These changes are homologous with sequences from other species (Turk & Bode (1991) each herein incorporated by reference). At least 7 clones of each recombinant form were sequenced.

The 3 recombinant forms were subcloned into the retroviral vector NIT for use in transient retroviral production (Pear et al. (1993) *Proc. Natl. Acad. Sci. USA* 90:8392–8396, each herein incorporated by reference). NIT is a Moloney murine leukemia virus-based retroviral vector with an expression cassette encoding a neomycin-resistance gene, an internal ribosomal entry site and the tetracycline transactivator. The transgene is expressed from a minimal CMV promoter containing 6-tandem tetracycline operators. At least 7 clones of each recombinant form were sequenced. AHPs were resuspended in N2 medium (1 ml) containing retrovirus and polybrene (2 $\mu$g/ml, Sigma) for 30 min at 37° C. The cells were cultured and selected with G418 (400 to 1,000 $\mu$g/ml). Recombinant proteins i+g+and i-g+were purified by submitting the CMs to Ni-NTA (Qiagen) and lentil-lectin affinity chromatographies. Recombinant i+g- was purified by submitting CM to Ni-NTA and papain affinity chromatographies. The eluents were dialyzed against tissue culture medium or 25 mM ammonium bicarbonate before lyophylisation. FGF-2-S (Ray et al. (1995)) was subcloned into the retroviral vector LPCX for use in transient retroviral production. LPCX is derived from retroviral vector LNCX (Genbank acc. M28247) through substitution of the neomycin with a puromycin resistance gene. The transgene is expressed from a CMV promoter. AHPs expressing cystatin variants were infected with LPCX-FGF-2-S, cultured and co-selected with G418 and puromycin (0.8 to 1 $\mu$g/ml). Transgene expression was characterized in both cystatin variants and FGF-2-S co-infected AHPs by RNA blot analysis (data not shown).

Figure 3D:
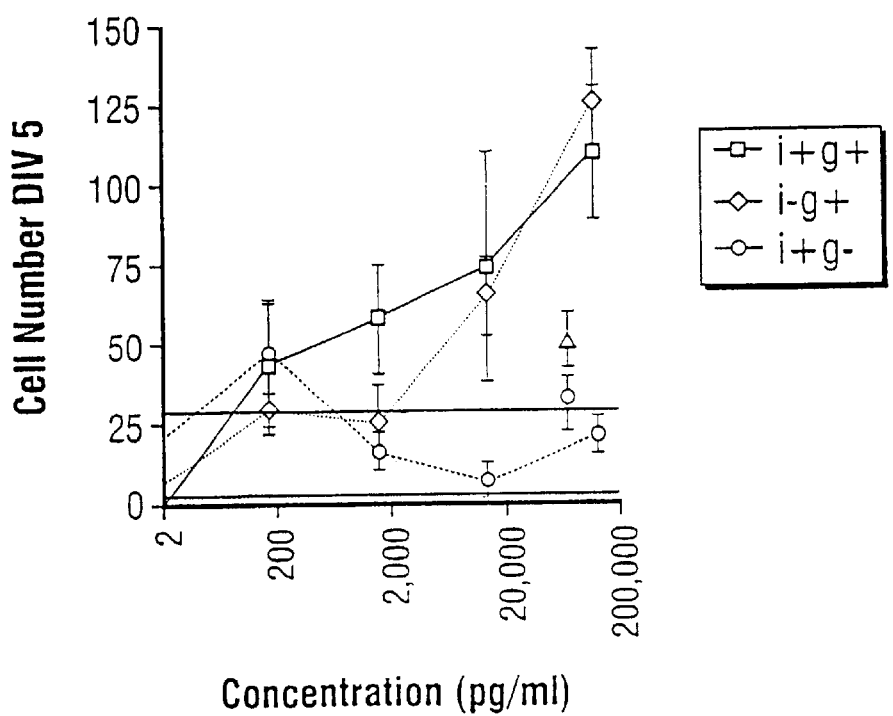

Protease inhibitor-deficient forms have been shown to lose their protease inhibitory activity and exist in vitro and in vivo (Machleidt et al. (1989)). On SDS-PAGE, the i+g+ form migrated at 16 kDa, the i-g+form at 17 kDa and the i+g- form, as reported for mouse cystatin C (Hakansson et al. (1996) *Comp. Biochem. Physiol.* 114:303–311, each herein incorporated by reference), at 12 kDa. The wild type form i+g+, at concentrations between 2 and 200 ng/ml in the presence of 20 ng/ml FGF-2, induced cell proliferation in a dose-dependent manner (FIG. 3d). While the protease inhibitor-deficient mutant (i–g+) retained the activity, the glycosylation-deficient form (i+g–) did not. The present data show that, whereas the N-linked carbohydrate moiety is necessary for the activity of CCg, the protease inhibitory domain is not directly involved. One-way ANOVA analysis of data (FIG. 3a) showed that there was a significant main effect due to treatments (F (2,6)=54.73, p<0.001), with significant increase in cell number with increasing concentration (F (6,12)=21.8, p<0.0001), as well as a significant concentration and treatment interaction (F (12,36)=6.23, p<0.0001). Specific comparisons showed significant differences (p<0.01) between all groups. For concentrations from 200 pg/ml and higher, there is also a significant main effect on treatments (F (3,8)=61.8, p<0.0001) and no significant differences between CCg-DG and CCg+chCystatin.

Example 4

Cloning of Neural Stem Cells In Vitro

We have previously cloned AHPs, and, showed that all three lineages are generated from single cells and that the cloned AHPs possess the capacity for self-renewal and retain their multilineage potential, defining the cloned cells as stem cells (Palmer et al. (1997) Mol. Cell. Neurosci. 8:389–404, each herein incorporated by reference). To investigate the ability of CCg to promote the proliferation and expansion of neural stem cells at clonal densities, single cells from previously cloned neural stem cells (Palmer et al. (1997)) were plated in N2, N2+FGF-2, N2+CCg and N2+FGF-2+ CCg (Table 2). While N2 alone did not support cell growth, in N2+FGF-2 or N2+CCg, 1% and 5% of single cells, respectively, grew clones to a maximum cell number of 55 before they died. In contrast, in the presence of FGF-2 and CCg, 31% of single cells expanded to a confluent population and were passaged. We have investigated the presence of tubulin-P III, a neuronal marker, O4, an oligodendrocytic marker, and glial fibrillary acidic protein (GFAP), an astrocytic marker, in the culture generated with FGF-2 and CCg. Less than 0.01% of the cells exhibited differentiated phenotypes and were astrocytes, no oligodendrocyte and no neuron were observed (data not shown), indicating that FGF-2 and CCg treatment does not differentiate AHPs toward any lineage.

To demonstrate the multipotentiality of the cloned cells, we analyzed two passaged clones after differentiation in the presence of retinoic acid (RA), a low concentration of FGF-2 and fetal bovine serum (FBS), known to differentiate neural stem and progenitor cells toward the neuronal lineage, the oligodendrocytic lineage and the astrocytic lineage, respectively (Palmer et al. (1997)). Both clones generated neurons, oligodendrocytes and astrocytes. Five percent of the cells were positive for tubulin-βIII, 0.5% for O4 and 8% for GFAP. Time lapse experiments were performed on single plated AHPs in the presence of FGF-2 and CCg. Each single cell produced two daughter cells, both undergoing cell division. Therefore, FGF-2 in the presence of CCg induces the cloned cells to undergo symmetrical division, defining the cloned cells as capable of self-renewal. Taken together these results show that in the presence of FGF-2 and CCg, the cloned cells retained their self-renewal and multipotential properties. CCg in association with FGF-2 could also induce proliferation of embryonic (E17) rat primary hippocampal neural progenitor cells plated at low density. Therefore, the cooperation of the two factors, FGF-2 and CCg, is needed for FGF-2-induced mitogenic activity on rat neural stem cells in vitro and for their expansion from a single cell.

Example 5

Stimulation of Neurogenesis In Vivo

To investigate the ability of CCg to stimulate neurogenesis, AHPs were genetically modified (Gage et al. (1995) Proc. Natl. Acad. Sci. USA) to co-express a secreted form of FGF-2 (FGF-2-S), constructed by fusing the pre-pro sequence of the human nerve growth factor (NGF) 5' to the rat FGF-2 sequence (Ray et al. (1995) J. Neurochem. 64:503–513, each herein incorporated by reference), and either the wild type form of CCg (i+g+) or the glycosylation-deficient form (i+g–). AHPs pre-labeled with fluorogold (FG) were grafted in adult rat hippocampus, a neurogenic region (Altman & Das (1965); Caviness, V. S. (1973); Eriksson et al. (1998)), and rats were injected with bromodeoxyuridine (BrdU), a thymidine analog that incorporates into the DNA of dividing cells and is used for birth-dating cells and monitoring cell proliferation (Kuhn et al. (1996)).

AHPs (75,000 cells in 1.5 $\mu$l), labeled for 4 h prior to grafting with FG (0.01%, Fluorochrome) (Erickson & Goins (1995) Development 121:915–924, each herein incorporated by reference), were stereotaxically injected into the hippocampus (anteroposterior axis –3.5, mediolateral axis ±3.0, dorsoventral axis –3.9 from skull, with nose bar at 5mm up) of anesthetized male Fischer–344 rats (200–220 g). Rats were administered daily injection of BrdU (50 mg/kg, Sigma) for 11 days following grafting. Then animals were sacrificed and perfused (4% paraformaldehyde) and 40 $\mu$m thick brain sections were cut on a freezing microtome. To assess the relevance of the use of FG to segregate the grated AHPs versus the endogenous cells, the following control experiments were performed. AHPs pre-labeled with FG were cultured up to 11 days in the presence of FGF-2. FG was still detectable in over 98% of the AHPs by immunocytochemistry (data not shown), suggesting that even after several cycles of division pre-labeled AHPs remained FG immunodetectable. Thus in the course of the in vivo experiment, AHPs pre-labeled with FG are likely to remain FG-positive. AHPs pre-labeled with FG were submitted to a few cycles of freezing and thawing; the resulting dead AHPs were grafted in the hippocampus where we detected no FG-positive cells and no increase in cell proliferation in the DG. Thus there was no transfer of FG to neighboring cells and the surgery did not have a non-specific effect on cell proliferation in the DG.

Figure 4A:
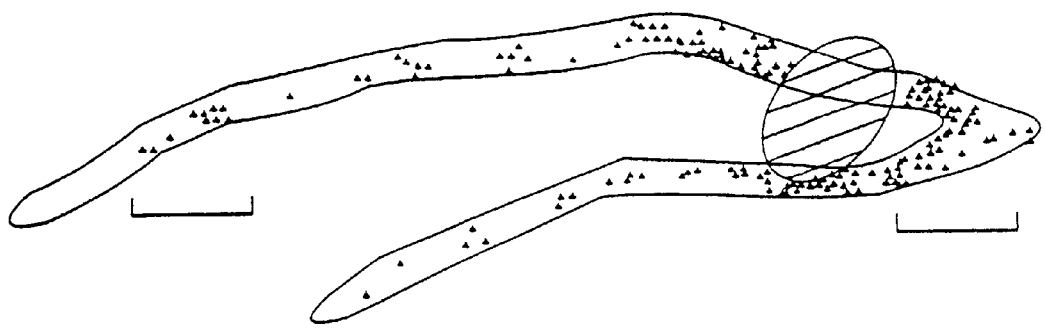
FIGS. 4A and 4B are camera lucida drawings of the distribution of BrdU-positive, FG-negative cells (red triangles), outside the graft area (blue line), in the DG of the hippocampus (purple line) grafted with AHPs co-expressing FGF-2-S and either i+g+(A) or i+g–(B). The quantification of newborn cells proximal to the grafts was performed within the subgranular layer of the DG, in a 280 μm area from the edge of the graft (black segment) and distal to the grafts in a 280 μm area beginning at least 800 μm from the tip of the graft.
Figure 4B:
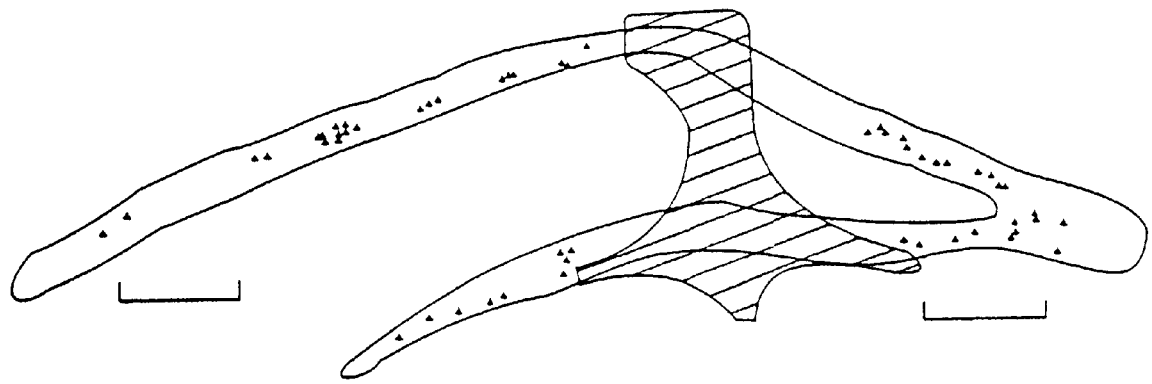
Figure 5A:
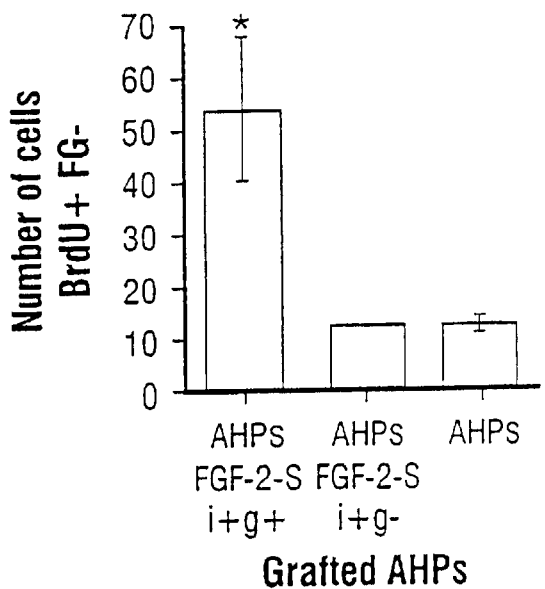
FIGS. 5A–5D are graphs illustrating the stimulation of neurogenesis in the adult rat DG by grafted AHPs co-expressing FGF-2-S and either the wild type form of CCg (i+g+) or the form of CCg with mutated N-glycosylation site (i+g–). Cell genesis was monitored at proximal (A, C) and distal (B, D) areas to the grafts, within the granular layer of the DG. An increase in tubulin-βIII-, BrdU-positive and FG-negative cells was only observed in the proximal area of the DG of the rats that received grafted AHPs co-expressing FGF-2-S and i+g+. An increase in tubulin-βIII-, BrdU-positive and FG-negative cells was only observed in the proximal area of the DG of the rats that received grafted AHPs co-expressing FGF-2-S and i+g+. Data are means ±s.e.m. for 4 animals in each treatment group (*$p<0.005$ by 2-way ANOVA).
Figure 5B:
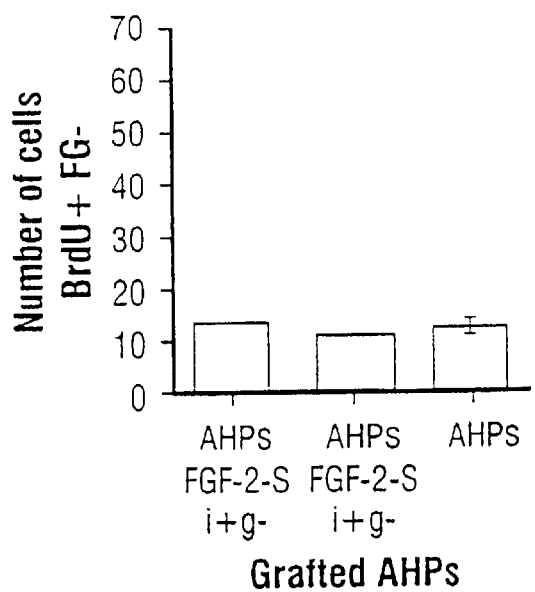
Figure 5C:
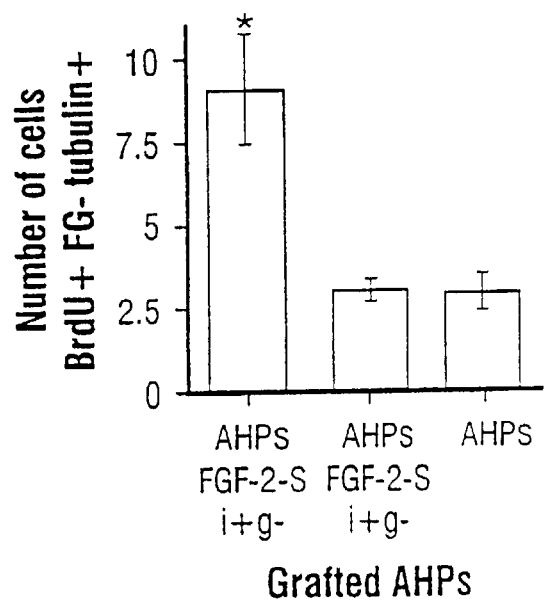
Figure 5D:
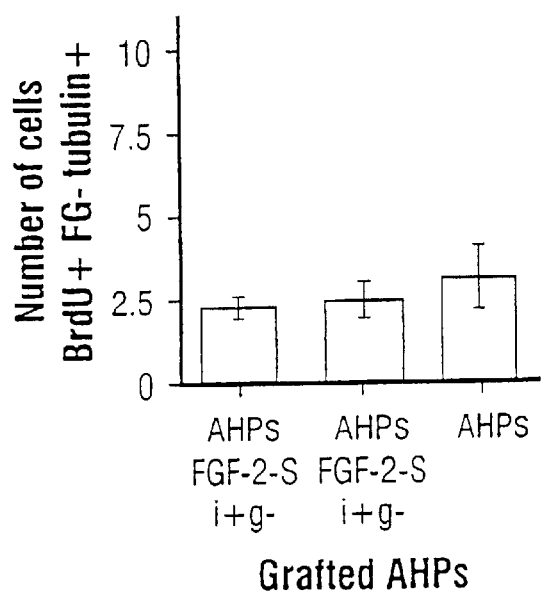

The proliferation of endogenous progenitor cells was determined immunohistochemically by counting the BrdU-positive and FG-negative cells. FG-positive cells and BrdU- and FG-positive cells were not included as they were derived from the grafts. Cell proliferation was monitored at proximal and distal areas to the grafts, within the granular layer of the DG (FIG. 4a and b). Eleven days after grafting, a four-fold increase in BrdU-positive and FG-negative cells was observed in the DG at the proximal areas of the grafted AHPs co-expressing FGF-2-S and i+g+ compared to the proximal areas where either AHPs co-expressing FGF-2-S and i+g– or AHPs were grafted (FIG. 5a). In contrast, at distal areas of the grafts, the numbers of BrdU-positive and FG-negative cells remained at their basal levels in all groups (FIG. 5b). The generation of new neurons was assessed by counting the tubulin-βIII-, BrdU-positive and FG-negative cells in the proximal and distal areas of the grafts (FIG. 5c and d). A four-fold increase in tubulin-βIII-, BrdU-positive and FG-negative cells was observed in the proximal areas of the grafted AHPs co-expressing FGF-2-S and i+g+, compared to all other groups. Our data indicate that FGF-2 and CCg cooperate to stimulate neurogenesis in the DG of the adult rat hippocampus and that the N-glycosylation of CCg is a requirement to stimulate neurogenesis in the presence of FGF-2.

The quantification of BrdU and tubulin-βIII cells proximal to the grafts was performed within the subgranular layer of the DG, 280 μm area from the edge of the graft in 4 sections using confocal scanning laser microscopy (Zeiss Axiovert and Biorad MRC1024). Similarly characterized cells distal to the grafts were counted in a 280 μm area beginning at least 800 μm from the tip of the graft (FIG. 4a and b). Immunofluorescence was performed (Gage et al. (1995) Proc. Natl. Acad. Sci. USA; Palmer et al. (1997)) with the following primary antibodies: tubulin-βIII (1/1,000, Sigma), GFAP (1/500, Adv. Immuno.), O4 (gift from O. Boegler), FG (1/2,000, Chemicon) and BrdU (1/100, Accurate). All secondary antibodies were from Jackson and streptavidin-biotin amplification was used when detecting FG. Protein concentrations were determined with Coomassie protein assay reagent (Pierce).

Group changes were assessed using one- and two-way ANOVA. When statistical differences were obtained at the $p<0.05$ level between groups, post hoc comparisons were made using the Fisher least squares difference (LSD) test. Student's t-test was used to make additional comparisons.

Although the invention has been described with reference to the presently preferred embodiment, it should be understood that various modifications can be made without departing from the spirit of the invention. Accordingly, the invention is limited only by the following claims.

What is claimed is:

1. A method of inducing proliferation of a mamnialian neuronal progenitor cell, comprising contacting said cell with fibroblast growth factor-2 (FGF-2) and glycosylated cystatin C (CCg) in an amount sufficient to induce cell proliferation.

2. The method of claim 1, wherein said contacting is in vitro.

3. The method of claim 1, wherein said contacting is in vivo.

4. The method of claim 1, wherein said contacting is ex vivo.

5. The method of claim 1, wherein said cell is a human progenitor cell.

6. A method of inducing proliferation of a mammalian neuronal progenitor cell, comprising: contacting said cell with full-length fibroblast growth factor-2, or a fragment thereof capable of inducing proliferation of said cell, and full-length glycosylated cystatin C (CCg), or a fragment thereof capable of augmenting the proliferating activity of fibroblast growth factor-2 on said cell, under conditions that induce cell proliferation.

7. The method of claim 6, wherein said cell is contacted with full-length glycosylated cystatin C.

8. The method of claim 6, wherein said cell is contacted with a full-length fibroblast growth factor.

9. The method of claim 6, wherein said cell is contacted with a full-length fibroblast growth factor-2.

10. The method of claim 6, wherein said cell is contacted in vitro.

11. The method of claim 6, wherein said cell is contacted in vivo.

12. The method of claim 6, wherein said cell is contacted ex vivo.

* * * * *